United States Patent
Feldman et al.

(10) Patent No.: US 12,048,530 B2
(45) Date of Patent: Jul. 30, 2024

(54) METHOD AND APPARATUS FOR DETECTING FALSE HYPOGLYCEMIC CONDITIONS

(71) Applicant: ABBOTT DIABETES CARE INC., Alameda, CA (US)

(72) Inventors: Benjamin Jay Feldman, Berkeley, CA (US); Adam Heller, Austin, TX (US); Namvar Kiaie, Danville, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 13 days.

(21) Appl. No.: 17/562,579

(22) Filed: Dec. 27, 2021

(65) Prior Publication Data
US 2022/0117523 A1    Apr. 21, 2022

Related U.S. Application Data

(60) Continuation of application No. 16/181,064, filed on Nov. 5, 2018, now Pat. No. 11,207,005, which is a (Continued)

(51) Int. Cl.
*A61B 5/145* (2006.01)
*A61B 5/00* (2006.01)
(Continued)

(52) U.S. Cl.
CPC .......... *A61B 5/14532* (2013.01); *A61B 5/01* (2013.01); *A61B 5/1451* (2013.01);
(Continued)

(58) Field of Classification Search
CPC ..... A61B 5/14532; A61B 5/01; A61B 5/1451; A61B 5/14546; A61B 5/14865; A61B 5/746
See application file for complete search history.

(56) References Cited

U.S. PATENT DOCUMENTS 3,581,062 A    5/1971    Aston
3,926,760 A    12/1975    Allen et al.
(Continued)

FOREIGN PATENT DOCUMENTS

DE    4401400    7/1995
EP    0098592    1/1984
(Continued)

OTHER PUBLICATIONS

U.S. Appl. No. 16/181,064 (U.S. Pat. No. 11,207,005), filed Nov. 5, 2018 (Dec. 28, 2021).
(Continued)

*Primary Examiner* — Eric J Messersmith
(74) *Attorney, Agent, or Firm* — Baker Botts L.L.P.

(57) ABSTRACT

Embodiments of the present disclosure include detecting a concurrent occurrence of a decrease in monitored analyte level and a corresponding decrease in monitored on-skin temperature, confirming a presence of an impending hypoglycemic condition, and asserting a notification corresponding to the confirmed impending hypoglycemic condition. Devices, methods, systems and kits incorporating the same are also provided.

21 Claims, 7 Drawing Sheets

Related U.S. Application Data continuation of application No. 14/730,077, filed on Jun. 3, 2015, now Pat. No. 10,117,606, which is a continuation of application No. 13/477,026, filed on May 21, 2012, now Pat. No. 9,050,041, which is a division of application No. 12/916,481, filed on Oct. 29, 2010, now Pat. No. 8,185,181.

(60) Provisional application No. 61/256,920, filed on Oct. 30, 2009.

(51) Int. Cl.
 *A61B 5/01* (2006.01)
 *A61B 5/1486* (2006.01)

(52) U.S. Cl.
 CPC ...... *A61B 5/14546* (2013.01); *A61B 5/14865* (2013.01); *A61B 5/746* (2013.01)

(56) References Cited

U.S. PATENT DOCUMENTS

| | | |
|---|---|---|
| 3,949,388 A | 4/1976 | Fuller |
| 3,960,497 A | 6/1976 | Acord et al. |
| 3,978,856 A | 9/1976 | Michel |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,441,968 A | 4/1984 | Emmer et al. |
| 4,462,048 A | 7/1984 | Ross |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,619,793 A | 10/1986 | Lee |
| 4,671,288 A | 6/1987 | Gough |
| 4,703,756 A | 11/1987 | Gough et al. |
| 4,711,245 A | 12/1987 | Higgins et al. |
| 4,731,051 A | 3/1988 | Fischell |
| 4,731,726 A | 3/1988 | Allen, III |
| 4,749,985 A | 6/1988 | Corsberg |
| 4,757,022 A | 7/1988 | Shults et al. |
| 4,759,366 A | 7/1988 | Callaghan |
| 4,777,953 A | 10/1988 | Ash et al. |
| 4,779,618 A | 10/1988 | Mund et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,947,845 A | 8/1990 | Davis |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,113,869 A | 5/1992 | Nappholz et al. |
| 5,122,925 A | 6/1992 | Inpyn |
| 5,135,004 A | 8/1992 | Adams et al. |
| 5,148,812 A | 9/1992 | Verrier et al. |
| 5,165,407 A | 11/1992 | Wilson et al. |
| 5,199,428 A | 4/1993 | Obel et al. |
| 5,202,261 A | 4/1993 | Musho et al. |
| 5,203,326 A | 4/1993 | Collins |
| 5,204,264 A | 4/1993 | Kaminer et al. |
| 5,210,778 A | 5/1993 | Massart |
| 5,231,988 A | 8/1993 | Wernicke et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,313,953 A | 5/1994 | Yomtov et al. |
| 5,320,715 A | 6/1994 | Berg |
| 5,320,725 A | 6/1994 | Gregg et al. |
| 5,322,063 A | 6/1994 | Allen et al. |
| 5,328,460 A | 7/1994 | Lord et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,365,426 A | 11/1994 | Siegel et al. |
| 5,372,427 A | 12/1994 | Padovani et al. |
| 5,376,070 A | 12/1994 | Purvis et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,400,795 A | 3/1995 | Murphy et al. |
| 5,408,999 A | 4/1995 | Singh et al. |
| 5,411,647 A | 5/1995 | Johnson et al. |
| 5,425,749 A | 6/1995 | Adams |
| 5,425,868 A | 6/1995 | Pedersen |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,520,191 A | 5/1996 | Karlsson et al. |
| 5,531,878 A | 7/1996 | Vadgama et al. |
| 5,543,326 A | 8/1996 | Heller et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,890 A | 5/1997 | Carter et al. |
| 5,640,954 A | 6/1997 | Pfeiffer et al. |
| 5,653,239 A | 8/1997 | Pompei et al. |
| 5,660,163 A | 8/1997 | Schulman et al. |
| 5,665,222 A | 9/1997 | Heller et al. |
| 5,711,001 A | 1/1998 | Bussan et al. |
| 5,711,861 A | 1/1998 | Ward et al. |
| 5,720,295 A | 2/1998 | Greenhut et al. |
| 5,733,259 A | 3/1998 | Valcke et al. |
| 5,735,285 A | 4/1998 | Albert et al. |
| 5,741,211 A | 4/1998 | Renirie et al. |
| 5,772,586 A | 6/1998 | Heinonen et al. |
| 5,785,660 A | 7/1998 | van Lake et al. |
| 5,791,344 A | 8/1998 | Schulman et al. |
| 5,792,065 A | 8/1998 | Xue et al. |
| 5,820,551 A | 10/1998 | Hill et al. |
| 5,822,715 A | 10/1998 | Worthington et al. |

(56) References Cited

U.S. PATENT DOCUMENTS

| | | | |
|---|---|---|---|
| 5,891,047 A | 4/1999 | Lander et al. |
| 5,899,855 A | 5/1999 | Brown |
| 5,914,026 A | 6/1999 | Blubaugh, Jr. et al. |
| 5,918,603 A | 7/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,957,854 A | 9/1999 | Besson et al. |
| 5,960,797 A | 10/1999 | Kramer et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,016,443 A | 1/2000 | Ekwall et al. |
| 6,021,350 A | 2/2000 | Mathson |
| 6,024,699 A | 2/2000 | Surwit et al. |
| 6,038,469 A | 3/2000 | Karlsson et al. |
| 6,049,727 A | 4/2000 | Crothall |
| 6,071,391 A | 6/2000 | Gotoh et al. |
| 6,073,031 A | 6/2000 | Helstab et al. |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,103,033 A | 8/2000 | Say et al. |
| 6,108,577 A | 8/2000 | Benser |
| 6,112,116 A | 8/2000 | Fischell |
| 6,115,622 A | 9/2000 | Minoz |
| 6,115,628 A | 9/2000 | Stadler et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,128,526 A | 10/2000 | Stadler et al. |
| 6,134,461 A | 10/2000 | Say et al. |
| 6,143,164 A | 11/2000 | Heller et al. |
| 6,144,837 A | 11/2000 | Quy |
| 6,159,147 A | 12/2000 | Lichter et al. |
| 6,161,095 A | 12/2000 | Brown |
| 6,162,611 A | 12/2000 | Heller et al. |
| 6,175,752 B1 * | 1/2001 | Say .................... A61B 5/1495 128/903 |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,233,471 B1 | 5/2001 | Berner et al. |
| 6,233,486 B1 | 5/2001 | Ekwall et al. |
| 6,248,067 B1 | 6/2001 | Causey, III et al. |
| 6,249,705 B1 | 6/2001 | Snell |
| 6,254,586 B1 | 7/2001 | Mann et al. |
| 6,256,538 B1 | 7/2001 | Ekwall |
| 6,264,606 B1 | 7/2001 | Ekwall et al. |
| 6,270,455 B1 | 8/2001 | Brown |
| 6,272,379 B1 | 8/2001 | Fischell et al. |
| 6,275,717 B1 | 8/2001 | Gross et al. |
| 6,283,761 B1 | 9/2001 | Joao |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,361,503 B1 | 3/2002 | Starobin et al. |
| 6,366,794 B1 | 4/2002 | Moussy et al. |
| 6,377,828 B1 | 4/2002 | Chaiken et al. |
| 6,377,852 B1 | 4/2002 | Bornzin et al. |
| 6,377,894 B1 | 4/2002 | Deweese et al. |
| 6,379,301 B1 | 4/2002 | Worthington et al. |
| 6,381,493 B1 | 4/2002 | Stadler et al. |
| 6,387,048 B1 | 5/2002 | Schulman et al. |
| 6,405,066 B1 | 6/2002 | Essenpreis et al. |
| 6,413,393 B1 | 7/2002 | Van Antwerp et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,471,689 B1 | 10/2002 | Joseph et al. |
| 6,478,736 B1 | 11/2002 | Mault |
| 6,484,046 B1 | 11/2002 | Say et al. |
| 6,501,983 B1 | 12/2002 | Natarajan et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,540,891 B1 | 4/2003 | Stewart et al. |
| 6,544,212 B2 | 4/2003 | Galley et al. |
| 6,551,494 B1 | 4/2003 | Heller et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,622,045 B2 | 9/2003 | Snell et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulsen et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciurczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,721,582 B2 | 4/2004 | Trepagnier et al. |
| 6,730,200 B1 | 5/2004 | Stewart et al. |
| 6,731,985 B2 | 5/2004 | Poore et al. |
| 6,733,446 B2 | 5/2004 | Lebel et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,773,671 B1 | 8/2004 | Lewis et al. |

(56) References Cited

U.S. PATENT DOCUMENTS

| | | |
|---|---|---|
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,912,413 B2 | 6/2005 | Rantala et al. |
| 6,923,763 B1 | 8/2005 | Kovatchev et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman IV et al. |
| 6,954,662 B2 | 10/2005 | Freger et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,010,345 B2 | 3/2006 | Hill et al. |
| 7,011,630 B2 | 3/2006 | Desai et al. |
| 7,016,713 B2 | 3/2006 | Gardner et al. |
| 7,016,720 B2 | 3/2006 | Kroll |
| 7,022,072 B2 | 4/2006 | Fox et al. |
| 7,022,219 B2 | 4/2006 | Mansouri et al. |
| 7,024,245 B2 | 4/2006 | Lebel et al. |
| 7,025,425 B2 | 4/2006 | Kovatchev et al. |
| 7,029,443 B2 | 4/2006 | Kroll |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,052,472 B1 | 5/2006 | Miller et al. |
| 7,052,483 B2 | 5/2006 | Wojcik |
| 7,056,302 B2 | 6/2006 | Douglas |
| 7,074,307 B2 | 7/2006 | Simpson et al. |
| 7,076,300 B1 | 7/2006 | Kroll et al. |
| 7,081,195 B2 | 7/2006 | Simpson et al. |
| 7,092,891 B2 | 8/2006 | Maus et al. |
| 7,096,064 B2 | 8/2006 | Deno et al. |
| 7,098,803 B2 | 8/2006 | Mann et al. |
| 7,103,412 B1 | 9/2006 | Kroll |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,134,999 B2 | 11/2006 | Brauker et al. |
| 7,136,689 B2 | 11/2006 | Shults et al. |
| 7,142,911 B2 | 11/2006 | Boileau et al. |
| 7,153,265 B2 | 12/2006 | Vachon |
| 7,167,818 B2 | 1/2007 | Brown |
| 7,171,274 B2 | 1/2007 | Starkweather et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,225,535 B2 | 6/2007 | Feldman et al. |
| 7,226,978 B2 | 6/2007 | Tapsak et al. |
| 7,258,673 B2 | 8/2007 | Racchini et al. |
| 7,267,665 B2 | 9/2007 | Steil et al. |
| 7,272,436 B2 | 9/2007 | Gill et al. |
| 7,276,029 B2 | 10/2007 | Goode, Jr. et al. |
| 7,278,983 B2 | 10/2007 | Ireland et al. |
| 7,295,867 B2 | 11/2007 | Berner et al. |
| 7,297,114 B2 | 11/2007 | Gill et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,402,153 B2 | 7/2008 | Steil et al. |
| 7,404,796 B2 | 7/2008 | Ginsberg |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,494,465 B2 | 2/2009 | Brister et al. |
| 7,497,827 B2 | 3/2009 | Brister et al. |
| 7,499,002 B2 | 3/2009 | Blasko et al. |
| 7,502,644 B2 | 3/2009 | Gill et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,524,287 B2 | 4/2009 | Bharmi |
| 7,547,281 B2 | 6/2009 | Hayes et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,620,438 B2 | 11/2009 | He |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,699,775 B2 | 4/2010 | Desai et al. |
| 7,699,964 B2 | 4/2010 | Feldman et al. |
| 7,711,493 B2 | 5/2010 | Bartkowiak et al. |
| 7,736,310 B2 | 6/2010 | Taub et al. |
| 7,751,864 B2 | 7/2010 | Buck, Jr. |
| 7,766,829 B2 | 8/2010 | Sloan et al. |
| 7,771,352 B2 | 8/2010 | Shults et al. |
| 7,774,145 B2 | 8/2010 | Brauker et al. |
| 7,778,680 B2 | 8/2010 | Goode, Jr. et al. |
| 7,826,981 B2 | 11/2010 | Goode, Jr. et al. |
| 7,857,760 B2 | 12/2010 | Brister et al. |
| 7,866,026 B1 | 1/2011 | Wang et al. |
| 7,885,697 B2 | 2/2011 | Brister et al. |
| 7,889,069 B2 | 2/2011 | Fifolt et al. |
| 7,899,511 B2 | 3/2011 | Shults et al. |
| 7,905,833 B2 | 3/2011 | Brister et al. |
| 7,914,450 B2 | 3/2011 | Goode, Jr. et al. |
| 7,920,906 B2 | 4/2011 | Goode et al. |
| 7,938,797 B2 | 5/2011 | Estes |
| 7,946,984 B2 | 5/2011 | Brister et al. |
| 7,974,672 B2 | 7/2011 | Shults et al. |
| 8,019,410 B1 * | 9/2011 | Bharmi ............... A61B 5/0205 600/365 |
| 8,060,173 B2 | 11/2011 | Goode, Jr. et al. |
| 8,116,837 B2 | 2/2012 | Huang |
| 8,140,312 B2 | 3/2012 | Hayter et al. |
| 8,160,900 B2 | 4/2012 | Taub et al. |
| 8,170,803 B2 | 5/2012 | Kamath et al. |
| 8,211,016 B2 | 7/2012 | Budiman |
| 8,216,137 B2 | 7/2012 | Budiman |
| 8,216,138 B1 | 7/2012 | McGarraugh et al. |
| 8,239,166 B2 | 8/2012 | Hayter et al. |
| 8,255,026 B1 | 8/2012 | Al-Ali |
| 8,282,549 B2 | 10/2012 | Brauker et al. |

(56) References Cited

U.S. PATENT DOCUMENTS

| | | |
|---|---|---|
| 8,376,945 B2 | 2/2013 | Hayter et al. |
| 8,444,560 B2 | 5/2013 | Hayter et al. |
| 8,457,703 B2 | 6/2013 | Al-Ali |
| 8,484,005 B2 | 7/2013 | Hayter et al. |
| 8,532,935 B2 | 9/2013 | Budiman |
| 8,543,354 B2 | 9/2013 | Luo et al. |
| 8,571,808 B2 | 10/2013 | Hayter |
| 8,612,163 B2 | 12/2013 | Hayter et al. |
| 8,657,746 B2 | 2/2014 | Roy |
| 8,682,615 B2 | 3/2014 | Hayter et al. |
| 9,060,719 B2 | 6/2015 | Hayter et al. |
| 9,113,828 B2 | 8/2015 | Budiman |
| 9,398,872 B2 | 7/2016 | Hayter et al. |
| 9,408,566 B2 | 8/2016 | Hayter et al. |
| 9,483,608 B2 | 11/2016 | Hayter et al. |
| 9,558,325 B2 | 1/2017 | Hayter et al. |
| 2001/0041831 A1 | 11/2001 | Starkweather et al. |
| 2002/0016534 A1 | 2/2002 | Trepagnier et al. |
| 2002/0019022 A1 | 2/2002 | Dunn et al. |
| 2002/0042090 A1 | 4/2002 | Heller et al. |
| 2002/0065454 A1 | 5/2002 | Lebel et al. |
| 2002/0068860 A1 | 6/2002 | Clark |
| 2002/0103499 A1 | 8/2002 | Perez et al. |
| 2002/0106709 A1* | 8/2002 | Potts ............... A61B 5/14532 435/14 |
| 2002/0120186 A1 | 8/2002 | Keimel |
| 2002/0128594 A1 | 9/2002 | Das et al. |
| 2002/0143266 A1 | 10/2002 | Bock |
| 2002/0143372 A1 | 10/2002 | Snell et al. |
| 2002/0156355 A1 | 10/2002 | Gough |
| 2002/0161288 A1 | 10/2002 | Shin et al. |
| 2002/0169635 A1 | 11/2002 | Shillingburg |
| 2002/0193679 A1 | 12/2002 | Malave et al. |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0065308 A1 | 4/2003 | Lebel et al. |
| 2003/0100821 A1 | 5/2003 | Heller et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0235817 A1 | 12/2003 | Bartkowiak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0077962 A1 | 4/2004 | Kroll |
| 2004/0078065 A1 | 4/2004 | Kroll |
| 2004/0093167 A1 | 5/2004 | Braig et al. |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0138716 A1 | 7/2004 | Kon et al. |
| 2004/0142403 A1 | 7/2004 | Hetzel et al. |
| 2004/0146909 A1 | 7/2004 | Duong et al. |
| 2004/0152622 A1 | 8/2004 | Keith et al. |
| 2004/0162678 A1 | 8/2004 | Hetzel et al. |
| 2004/0167801 A1 | 8/2004 | Say et al. |
| 2004/0171921 A1 | 9/2004 | Say et al. |
| 2004/0172307 A1 | 9/2004 | Gruber |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0204687 A1 | 10/2004 | Mogensen et al. |
| 2004/0208780 A1 | 10/2004 | Faries, Jr. et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0249420 A1 | 12/2004 | Olson et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0263354 A1 | 12/2004 | Mann et al. |
| 2004/0267300 A1 | 12/2004 | Mace |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0010269 A1 | 1/2005 | Lebel et al. |
| 2005/0016276 A1 | 1/2005 | Guan et al. |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0049473 A1 | 3/2005 | Desai et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0114068 A1 | 5/2005 | Chey et al. |
| 2005/0115832 A1 | 6/2005 | Simpson et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0196821 A1 | 9/2005 | Monfre et al. |
| 2005/0199494 A1 | 9/2005 | Say et al. |
| 2005/0203360 A1 | 9/2005 | Brauker et al. |
| 2005/0214892 A1 | 9/2005 | Kovatchev et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0277164 A1 | 12/2005 | Drucker et al. |
| 2005/0277912 A1 | 12/2005 | John |
| 2005/0287620 A1 | 12/2005 | Heller et al. |
| 2005/0288725 A1 | 12/2005 | Hettrick et al. |
| 2006/0001538 A1 | 1/2006 | Kraft et al. |
| 2006/0004270 A1 | 1/2006 | Bedard et al. |

(56) References Cited

U.S. PATENT DOCUMENTS

| | | |
|---|---|---|
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025662 A1 | 2/2006 | Buse et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0091006 A1 | 5/2006 | Wang et al. |
| 2006/0142651 A1 | 6/2006 | Brister et al. |
| 2006/0155180 A1 | 7/2006 | Brister et al. |
| 2006/0166629 A1 | 7/2006 | Reggiardo |
| 2006/0167365 A1 | 7/2006 | Bharmi |
| 2006/0167517 A1 | 7/2006 | Gill et al. |
| 2006/0167518 A1 | 7/2006 | Gill et al. |
| 2006/0167519 A1 | 7/2006 | Gill et al. |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0193375 A1 | 8/2006 | Lee |
| 2006/0222566 A1 | 10/2006 | Brauker et al. |
| 2006/0224109 A1 | 10/2006 | Steil et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247685 A1 | 11/2006 | Bharmi |
| 2006/0247985 A1 | 11/2006 | Liamos et al. |
| 2006/0258929 A1 | 11/2006 | Goode et al. |
| 2006/0264785 A1 | 11/2006 | Dring et al. |
| 2006/0272652 A1 | 12/2006 | Stocker et al. |
| 2006/0281985 A1 | 12/2006 | Ward et al. |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0095661 A1 | 5/2007 | Wang et al. |
| 2007/0106135 A1 | 5/2007 | Sloan et al. |
| 2007/0108048 A1 | 5/2007 | Wang et al. |
| 2007/0118030 A1 | 5/2007 | Bruce et al. |
| 2007/0118405 A1 | 5/2007 | Campbell et al. |
| 2007/0124002 A1 | 5/2007 | Estes et al. |
| 2007/0129621 A1 | 6/2007 | Kellogg et al. |
| 2007/0149875 A1 | 6/2007 | Ouyang et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179434 A1 | 8/2007 | Weinert et al. |
| 2007/0191701 A1 | 8/2007 | Feldman et al. |
| 2007/0197889 A1* | 8/2007 | Brister ............... A61B 5/15142 600/347 |
| 2007/0199818 A1 | 8/2007 | Petyt et al. |
| 2007/0202562 A1 | 8/2007 | Curry et al. |
| 2007/0203407 A1 | 8/2007 | Hoss et al. |
| 2007/0203966 A1 | 8/2007 | Brauker et al. |
| 2007/0213657 A1 | 9/2007 | Jennewine et al. |
| 2007/0227911 A1 | 10/2007 | Wang et al. |
| 2007/0232877 A1 | 10/2007 | He |
| 2007/0232878 A1 | 10/2007 | Kovatchev et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0249922 A1 | 10/2007 | Peyser et al. |
| 2007/0255321 A1 | 11/2007 | Gerber et al. |
| 2007/0282299 A1 | 12/2007 | Hellwig |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0012701 A1 | 1/2008 | Kass et al. |
| 2008/0017522 A1 | 1/2008 | Heller et al. |
| 2008/0021666 A1 | 1/2008 | Goode, Jr. et al. |
| 2008/0021972 A1 | 1/2008 | Huelskamp et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0066305 A1 | 3/2008 | Wang et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0102441 A1 | 5/2008 | Chen et al. |
| 2008/0108942 A1 | 5/2008 | Brister et al. |
| 2008/0119703 A1 | 5/2008 | Brister et al. |
| 2008/0119708 A1 | 5/2008 | Budiman |
| 2008/0139910 A1 | 6/2008 | Mastrototaro et al. |
| 2008/0148873 A1 | 6/2008 | Wang |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |

(56) References Cited

U.S. PATENT DOCUMENTS

| | | |
|---|---|---|
| 2008/0201325 A1 | 8/2008 | Doniger et al. |
| 2008/0208025 A1 | 8/2008 | Shults et al. |
| 2008/0208113 A1 | 8/2008 | Damiano et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234943 A1 | 9/2008 | Ray et al. |
| 2008/0242961 A1 | 10/2008 | Brister et al. |
| 2008/0242963 A1 | 10/2008 | Essenpreis et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0275313 A1 | 11/2008 | Brister et al. |
| 2008/0278332 A1 | 11/2008 | Fennell et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0030641 A1 | 1/2009 | Fjield et al. |
| 2009/0033333 A1* | 2/2009 | Gribova .................. A61B 5/30 324/439 |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054748 A1 | 2/2009 | Feldman et al. |
| 2009/0054749 A1 | 2/2009 | He |
| 2009/0054753 A1 | 2/2009 | Robinson et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0069649 A1 | 3/2009 | Budiman |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0099436 A1 | 4/2009 | Brister et al. |
| 2009/0105560 A1 | 4/2009 | Solomon |
| 2009/0105570 A1 | 4/2009 | Sloan et al. |
| 2009/0105636 A1 | 4/2009 | Hayter et al. |
| 2009/0112478 A1 | 4/2009 | Mueller, Jr. et al. |
| 2009/0112626 A1 | 4/2009 | Talbot et al. |
| 2009/0118589 A1 | 5/2009 | Ueshima et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0143725 A1 | 6/2009 | Peyser et al. |
| 2009/0149728 A1 | 6/2009 | Van Antwerp et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0182517 A1 | 7/2009 | Gandhi et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0253973 A1 | 10/2009 | Bashan et al. |
| 2009/0257911 A1 | 10/2009 | Thomas et al. |
| 2009/0281407 A1 | 11/2009 | Budiman |
| 2009/0287073 A1 | 11/2009 | Boock et al. |
| 2009/0287074 A1 | 11/2009 | Shults et al. |
| 2009/0294277 A1 | 12/2009 | Thomas et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063372 A1 | 3/2010 | Potts et al. |
| 2010/0064764 A1 | 3/2010 | Hayter et al. |
| 2010/0081909 A1 | 4/2010 | Budiman et al. |

(56) References Cited

U.S. PATENT DOCUMENTS

| | | |
|---|---|---|
| 2010/0081953 A1 | 4/2010 | Syeda-Mahmood et al. |
| 2010/0121167 A1 | 5/2010 | McGarraugh et al. |
| 2010/0141656 A1 | 6/2010 | Krieftewirth |
| 2010/0152561 A1 | 6/2010 | Goodnow et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0191085 A1 | 7/2010 | Budiman |
| 2010/0198034 A1 | 8/2010 | Thomas et al. |
| 2010/0198142 A1 | 8/2010 | Sloan et al. |
| 2010/0204557 A1 | 8/2010 | Kiaie et al. |
| 2010/0213057 A1 | 8/2010 | Feldman et al. |
| 2010/0234710 A1 | 9/2010 | Budiman et al. |
| 2010/0261987 A1 | 10/2010 | Kamath et al. |
| 2010/0280441 A1 | 11/2010 | Wilinska et al. |
| 2010/0312176 A1 | 12/2010 | Lauer et al. |
| 2010/0313105 A1 | 12/2010 | Nekoomaram et al. |
| 2010/0317952 A1* | 12/2010 | Budiman ............. A61B 5/4839 600/365 |
| 2010/0324392 A1 | 12/2010 | Yee et al. |
| 2010/0326842 A1 | 12/2010 | Mazza et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0029247 A1 | 2/2011 | Kalathil |
| 2011/0040163 A1 | 2/2011 | Telson et al. |
| 2011/0060530 A1 | 3/2011 | Fennell |
| 2011/0077490 A1 | 3/2011 | Simpson et al. |
| 2011/0077494 A1 | 3/2011 | Doniger et al. |
| 2011/0082484 A1 | 4/2011 | Saravia et al. |
| 2011/0106126 A1 | 5/2011 | Love et al. |
| 2011/0112696 A1 | 5/2011 | Yodfat et al. |
| 2011/0148905 A1 | 6/2011 | Simmons et al. |
| 2011/0208027 A1 | 8/2011 | Wagner et al. |
| 2011/0208155 A1 | 8/2011 | Palerm et al. |
| 2011/0257895 A1 | 10/2011 | Brauker et al. |
| 2011/0263958 A1 | 10/2011 | Brauker et al. |
| 2011/0320130 A1 | 12/2011 | Valdes et al. |
| 2012/0078071 A1 | 3/2012 | Bohm et al. |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0209099 A1 | 8/2012 | Ljuhs et al. |
| 2012/0215462 A1 | 8/2012 | Goode et al. |
| 2012/0277565 A1 | 11/2012 | Budiman |
| 2012/0283542 A1 | 11/2012 | McGarraugh |
| 2012/0318670 A1 | 12/2012 | Karinka et al. |
| 2013/0035575 A1 | 2/2013 | Mayou et al. |
| 2013/0137953 A1 | 5/2013 | Harper et al. |
| 2013/0231541 A1 | 9/2013 | Hayter et al. |
| 2013/0324823 A1 | 12/2013 | Koski et al. |
| 2014/0005499 A1 | 1/2014 | Catt et al. |
| 2014/0046160 A1 | 2/2014 | Terashima et al. |
| 2014/0088392 A1 | 3/2014 | Bernstein et al. |
| 2014/0121488 A1 | 5/2014 | Budiman |
| 2014/0221966 A1 | 8/2014 | Buckingham et al. |
| 2015/0216456 A1 | 8/2015 | Budiman |
| 2015/0241407 A1 | 8/2015 | Ou et al. |
| 2015/0366510 A1 | 12/2015 | Budiman |
| 2016/0022221 A1 | 1/2016 | Ou et al. |
| 2016/0302701 A1 | 10/2016 | Bhavaraju et al. |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0472411 | 2/1992 |
| EP | 0286118 | 1/1995 |
| EP | 0867146 | 9/1998 |
| EP | 1048264 | 11/2000 |
| EP | 1419731 | 5/2004 |
| EP | 0939602 | 9/2004 |
| EP | 1850909 | 4/2010 |
| EP | 1677668 | 7/2010 |
| JP | 2004-358261 | 12/2004 |
| WO | WO-1996/025089 | 8/1996 |
| WO | WO-1996/035370 | 11/1996 |
| WO | WO-1997/015227 | 5/1997 |
| WO | WO-1998/035053 | 8/1998 |
| WO | WO-1999/056613 | 11/1999 |
| WO | WO-2000/049940 | 8/2000 |
| WO | WO-2000/059370 | 10/2000 |
| WO | WO-2000/074753 | 12/2000 |
| WO | WO-2000/078992 | 12/2000 |
| WO | WO-2001/052935 | 7/2001 |
| WO | WO-2001/054753 | 8/2001 |
| WO | WO-2002/016905 | 2/2002 |
| WO | WO-2002/058537 | 8/2002 |
| WO | WO-2003/076893 | 9/2003 |
| WO | WO-2003/082091 | 10/2003 |
| WO | WO-2003/085372 | 10/2003 |
| WO | WO-2004/060455 | 7/2004 |
| WO | WO-2004/061420 | 7/2004 |
| WO | WO-2005/041766 | 5/2005 |
| WO | WO-2005/065542 | 7/2005 |
| WO | WO-2005/089103 | 9/2005 |
| WO | WO-2006/024671 | 3/2006 |
| WO | WO-2006/079114 | 7/2006 |
| WO | WO-2006/081336 | 8/2006 |
| WO | WO-2006/086423 | 8/2006 |
| WO | WO-2006/118947 | 11/2006 |
| WO | WO-2008/086541 | 7/2008 |

OTHER PUBLICATIONS

U.S. Appl. No. 14/730,077 (U.S. Pat. No. 10,117,606), filed Jun. 3, 2015 (Nov. 6, 2018).

U.S. Appl. No. 13/477,026 (U.S. Pat. No. 9,050,041), filed May 21, 2012 (Jun. 9, 2015).

U.S. Appl. No. 12/916,481 (U.S. Pat. No. 8,185,181), filed Oct. 29, 2010 (May 22, 2012).

U.S. Appl. No. 16/181,064, Nov. 19, 2021 Issue Fee Payment.

U.S. Appl. No. 16/181,064, Aug. 20, 2021 Notice of Allowance.

U.S. Appl. No. 16/181,064, Jun. 17, 2021 Response to Final Office Action and Request for Continued Examination (RCE).

U.S. Appl. No. 16/181,064, Mar. 29, 2021 Final Office Action.

U.S. Appl. No. 16/181,064, Dec. 21, 2020 Response to Non-Final Office Action.

U.S. Appl. No. 16/181,064, Sep. 22, 2020 Non-Final Office Action.

Armour, J. C., et al., "Application of Chronic Intravascular Blood Glucose Sensor in Dogs", Diabetes, vol. 39, 1990, pp. 1519-1526.

Bennion, N., et al., "Alternate Site Glucose Testing: A Crossover Design", Diabetes Technology & Therapeutics, vol. 4, No. 1, 2002, pp. 25-33.

Blendea, M. C., et al., "Heart Disease in Diabetic Patients", Current Diabetes Reports, vol. 3, 2003, pp. 223-229.

Brooks, S. L., et al., "Development of an On-Line Glucose Sensor for Fermentation Monitoring", Biosensors, vol. 3, 1987/1988, pp. 45-56.

Cass, A. E., et al., "Ferrocene-Medicated Enzyme Electrode for Amperometric Determination of Glucose", Analytical Chemistry, vol. 56, No. 4, 1984, 667-671.

Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.

Dassau, E., et al., "Detection of a Meal Using Continuous Glucose Monitoring", Emerging Treatments and Technologies, vol. 31, No. 2, Feb. 2008, pp. 295-300.

(56) References Cited

OTHER PUBLICATIONS

Diabetes Control and Complications Trial Research Group, "The Effect of Intensive Treatment of Diabetes on the Development and Progression of Long-Term Complications in Insulin-Dependent Diabetes Mellitus," New England J. Med. vol. 329, 1993, pp. 977-986.

Eckert, B. et al. "Hypoglycaemia Leads to an Increased QT Interval in Normal Men," Clinical Physiology, vol. 18, No. 6, 1998, pp. 570-575.

Feldman, B., et al., "A Continuous Glucose Sensor Based on Wired EnzymeTM Technology—Results from a 3-Day Trial in Patients with Type 1 Diabetes", Diabetes Technology & Therapeutics, vol. 5, No. 5, 2003, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.

Georgescu, B., et al., "Real-Time Multimodel Tracking of Myocardium in Echocardiography Using Robust Information Fusion", Medical Image Computing and Computer-Assisted Intervention, 2004, pp. 777-785.

Goldman, J. M., et al., "Masimo Signal Extraction Pulse Oximetry", Journal of Clinical Monitoring and Computing, vol. 16, No. 7, 2000, pp. 475-483.

Harris, N.D., et al., "Can Changes in QT Interval be Used to Predict the Onset of Hypoglycemia in Type 1 Diabetes?", Computers in Cardiology, vol. 27, 2000, pp. 375-378.

Heller, S. R., "Abnormalities of the Electrocardiogram During Hypoglycemia: The Cause of the Dead in Bed Syndrome?" International Journal of Clinical Practice, Suppl. No. 129, 2002, pp. 27-32.

Hovorka, R., et al., "Nonlinear Model Predictive Control of Glucose Concentration in Subjects with Type 1 Diabetes", Physiological Measurement, vol. 55, Jul. 2004, pp. 905-920.

Hyunjin, L., et al., "A Closed-Loop Artificial Pancreas Using Model Predictive Control and a Sliding Meal Size Estimator", Journal of Diabetes Science and Technology, vol. 3, Issue 5, Sep. 2009, pp. 1082-1090.

Isermann, R., "Supervision, Fault-Detection and Fault-Diagnosis Methods—An Introduction", Control Engineering Practice, vol. 5, No. 5, 1997, pp. 639-652.

Isermann, R., et al., "Trends in the Application of Model-Based Fault Detection and Diagnosis of Technical Processes", Control Engineering Practice, vol. 5, No. 5, 1997, pp. 709-719.

Johnson, P. C., "Peripheral Circulation", John Wiley & Sons, 1978, pp. 198.

Jones, T. W., et al., "Mild Hypoglycemia and Impairment of Brain Stem and Cortical Evoked Potentials in Healthy Subjects," Diabetes vol. 39, 1990, 1550-1555.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", Diabetes Care, vol. 24, No. 7, 2001, pp. 1303-1304.

Kaplan, S. M., "Wiley Electrical and Electronics Engineering Dictionary", IEEE Press, 2004, pp. 141, 142, 548, 549.

Kovatchev, B. P., et al., "Graphical and Numerical Evaluation of Continuous Glucose Sensing Time Lag", Diabetes Technology & Therapeutics, vol. 11, No. 3, Feb. 2009, pp. 139-143.

Landstedt-Hallin, L., et al., "Increased QT Dispersion During Hypoglycaemia in Patients with Type 2 Diabetes Mellitus," Journal of Internal Medicine, vol. 246, 1999, 299-307.

Lortz, J., et al., "What is Bluetooth? We Explain The Newest Short-Range Connectivity Technology", Smart Computing Learning Series, Wireless Computing, vol. 8, Issue 5, 2002, pp. 72-74.

Maher, "A Method for Extrapolation of Missing Digital Audio Data", Preprints of Papers Presented at the AES Convention, 1993, pp. 1-19.

Maher, "Audio Enhancement using Nonlinear Time-Frequency Filtering", AES 26th International Conference, 2005, pp. 1-9.

Malin, S. F., et al., "Noninvasive Prediction of Glucose by Near-Infrared Diffuse Reflectance Spectoscopy", Clinical Chemistry, vol. 45, No. 9, 1999, pp. 1651-1658.

Malmberg, K., "Prospective Randomised Study of Intensive Insulin Treatment on Long-Term Survival After Acute Myocardial Infarction in Patients with Diabetes Mellitus", British Medical Journal, vol. 314, 1997, pp. 1512-1515.

Markel, A. et al, "Hypoglycaemia-Induced Ischaemic ECG Changes", Presse Medicale, vol. 23, No. 2, 1994, pp. 78-79.

Mcgarraugh, G., et al., "Glucose Measurements Using Blood Extracted from the Forearm and the Finger", TheraSense, Inc., 2001, 16 Pages.

Mcgarraugh, G., et al., "Physiological Influences on Off-Finger Glucose Testing", Diabetes Technology & Therapeutics, vol. 3, No. 3, 2001, pp. 367-376.

Mckean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.

Morbiducci, U, et al., "Improved Usability of the Minimal Model of Insulin Sensitivity Based on an Automated Approach and Genetic Algorithms for Parameter Estimation", Clinical Science, vol. 112, 2007, pp. 257-263.

Okin, P. M., et al, "Electrocardiographic Repolarization Complexity and Abnormality Predict All-Cause and Cardiovascular Mortality in Diabetes," Diabetes, vol. 53, 2004, pp. 434-440.

Peterson, K., et al., "Regulation of Serum Potassium During Insulin-Induced Hypoglycemia," Diabetes, vol. 31, 1982, pp. 615-617.

Pickup, J., et al., "Implantable Glucose Sensors: Choosing the Appropriate Sensing Strategy", Biosensors, vol. 3, 1987/1988, pp. 335-346.

Pickup, J., et al., "In Vivo Molecular Sensing in Diabetes Mellitus: An Implantable Glucose Sensor with Direct Electron Transfer", Diabetologia, vol. 32, 1989, pp. 213-217.

Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", The American Physiological Society, 1995, E155-E161.

Rana, B. S., et al., "Relation of QT Interval Dispersion to the Number of Different Cardiac Abnormalities in Diabetes Mellitus", The American Journal of Cardiology, vol. 90, 2002, pp. 483-487.

Robinson, R. T. C. E., et al. "Changes in Cardiac Repolarization During Clinical Episodes of Nocturnal Hypoglycaemia in Adults with Type 1 Diabetes," Diabetologia, vol. 47, 2004, pp. 312-315.

Roe, J. N., et al., "Bloodless Glucose Measurements", Critical Review in Therapeutic Drug Carrier Systems, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", Artificial Organs Today, vol. 2, No. 2, 1992, pp. 145-158.

Sakakida, M., et al., "Ferrocene-Mediated Needle-Type Glucose Sensor Covered with Newly Designed Biocompatible Membrane", Sensors and Actuators B, vol. 13-14, 1993, pp. 319-322.

Salehi, C., et al., "A Telemetry-Instrumentation System for Long-Term Implantable Glucose and Oxygen Sensors", Analytical Letters, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.

Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.

Shichiri, M., et al., "Glycaemic Control in Pancreatectomized Dogs with a Wearable Artificial Endocrine Pancreas", Diabetologia, vol. 24, 1983, pp. 179-184.

(56) References Cited

OTHER PUBLICATIONS

Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.

Shichiri, M., et al., "Membrane Design for Extending the Long-Life of an Implantable Glucose Sensor", Diabetes Nutrition and Metabolism, vol. 2, 1989, pp. 309-313.

Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.

Shichiri, M., et al., "Wearable Artificial Endocrine Pancreas With Needle-Type Glucose Sensor", The Lancet, 1982, pp. 1129-1131.

Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.

Steil, G. M., et al., "Closed-Loop Insulin Delivery—the Path of Physiological Glucose Control", Advanced Drug Delivery Reviews, vol. 56, 2004, pp. 125-144.

Steil, G. M., et al., "Determination of Plasma Glucose During Rapid Glucose Excursions with a Subcutaneous Glucose Sensor", Diabetes Technology & Therapeutics, vol. 5, No. 1, 2003, pp. 27-31.

Steinhaus, B. M., et al., "The Information Content of the Cardiac Electrogram at the Stimulus Site," Annual International Conference of the IEEE Engineering in Medicine and Biology Society, vol. 12, No. 2, 1990, 0607-0609.

Sternberg, R., et al., "Study and Development of Multilayer Needle-Type Enzyme-Based Glucose Microsensors", Biosensors, vol. 4, 1988, pp. 27-40.

Thompson, M., et al., "In Vivo Probes: Problems and Perspectives", Clinical Biochemistry, vol. 19, 1986, pp. 255-261.

Turner, A., et al., "Diabetes Mellitus: Biosensors for Research and Management", Biosensors, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117-137.

Velho, G., et al., "Strategies for Calibrating a Subcutaneous Glucose Sensor", Biomedica Biochimica Acta, vol. 48, 1989, pp. 957-964.

Whipple, G., "Low Residual Noise Speech Enhancement Utilizing Time-Frequency", Proceedings of the International Conference on Acoustics, Speech, and Signal Processing, vol. 19, 1994, pp. I5-I8.

Wilson, G. S., et al., "Progress Toward the Development of an Implantable Sensor for Glucose", Clinical Chemistry, vol. 38, No. 9, 1992, pp. 1613-1617.

Wolfe, P. J., et al., "Interpolation of Missing Data Values for Audio Signal Restoration Using a Gabor Regression Model", 2005 IEEE International Conference on Acoustics, Speech, and Signal Processing, vol. 5, 2005, pp. 517-520.

European Patent Application No. 10827587.6, Examination Report mailed Jul. 20, 2018.

PCT Application No. PCT/US2010/054879, International Preliminary Report on Patentability and Written Opinion of the International Searching Authority mailed May 10, 2012.

PCT Application No. PCT/US2010/054879, International Search Report and Written Opinion of The International Searching Authority mailed Dec. 27, 2010.

U.S. Appl. No. 12/916,481, Notice of Allowance Mar. 7, 2012.
U.S. Appl. No. 12/916,481, Office Action mailed Dec. 19, 2011.
U.S. Appl. No. 13/477,026, Advisory Action mailed Mar. 18, 2015.
U.S. Appl. No. 13/477,026, Notice of Allowance mailed Apr. 15, 2015.
U.S. Appl. No. 13/477,026, Office Action mailed Aug. 20, 2014.
U.S. Appl. No. 13/477,026, Office Action mailed Dec. 3, 2014.
U.S. Appl. No. 14/730,077, Notice of Allowance mailed Jul. 17, 2018.
U.S. Appl. No. 14/730,077, Office Action mailed Oct. 6, 2017.

\* cited by examiner

METHOD AND APPARATUS FOR DETECTING FALSE HYPOGLYCEMIC CONDITIONS

RELATED APPLICATION

The present application is a continuation of U.S. patent application Ser. No. 16/181,064 filed Nov. 5, 2018, which is a continuation of U.S. patent application Ser. No. 14/730,077 filed Jun. 3, 2015, now U.S. Pat. No. 10,117,606, which is a continuation of U.S. patent application Ser. No. 13/477,026 filed May 21, 2012, now U.S. Pat. No. 9,050,041, which is a divisional of U.S. patent application Ser. No. 12/916,481 filed Oct. 29, 2010, now U.S. Pat. No. 8,185,181, which claims the benefit of U.S. Provisional Application No. 61/256,920 filed Oct. 30, 2009, entitled "Method and Apparatus for Detecting False Hypoglycemic Conditions", the disclosures of each of which are incorporated herein by reference for all purposes.

BACKGROUND

For diabetic patients, it is desirable and often necessary to detect symptoms related to hypoglycemic condition, or the onset of such condition. If not treated in a timely manner, hypoglycemia (or commonly associated with low blood sugar level and sometimes referred to as "insulin shock") will have detrimental if not lethal effect on the patient. As insulin therapy becomes more prevalent for the treatment of diabetes mellitus, the detection of the onset of such conditions is significant.

When a diabetic person experiences hypoglycemic condition, often, the person will experience increased heart rate, perspiration, involuntary shaking, rapid decline in body temperature, paleness, and over the course of a period of hours, the declining blood sugar level may impact the brain functions, potentially resulting in dizziness, hindered bodily coordination, undesirable modification in behavior and the like. Death or permanent brain damage is not uncommon if the declining blood sugar level is left untreated.

Commercially available continuous glucose monitoring systems provide tools for diabetic patients to continuously monitor the glucose levels and provide on-going feedback to the patient to take corrective action. Such systems use glucose sensors which at times exhibit inaccuracies. That is, there are times when the glucose sensor may falsely indicate a low glucose reading, triggering a false warning to the user. The false indications, sometimes referred to as sensor signal dropouts, may be attributable to a variety of factors, such as inherent inaccuracies in the system, the instability of the sensor during the initial time period of use, changes in the sensor's environment, pressure on a blood vessel supplying glucose to the tissue in which the sensor is implanted, noise in the system, and the like. It has been found that such false positive indication of low glucose readings generated by the sensor in use occur more often during night time. This in turn causes a significant inconvenience or disadvantage to the user or the patient if alarms or notifications are associated with low glucose measurements and are triggered during night time, when in fact the glucose level of the patient or the user is not low and the triggered alarm or notification was a false alarm.

SUMMARY

In view of the foregoing, in aspects of the present disclosure, methods, systems, apparatus and kits are provided which reduce the occurrence of false alarms or notifications to the user associated with false hypoglycemic condition detection based on data from analyte sensors. In particular, in aspects of the present disclosure, a user's glucose level is monitored in conjunction with the temperature and/or perspiration level of the patient, and the fluctuations of the glucose level and the temperature and/or perspiration level is monitored such that, when a potential hypoglycemic condition or a potential impending hypoglycemic condition is detected, the presence of such potential conditions is confirmed before the associated notification or alarm is asserted.

In addition to the monitored temperature or perspiration level, within the scope of the present disclosure, other physiological parameters may be monitored for confirming the presence of hypoglycemic condition, such as, for example, a user's heart rate, detected tremor, or oxygen saturation level of the user's blood.

A method in accordance with one embodiment includes receiving a plurality of time spaced analyte related data monitored by an analyte sensor in fluid contact with an analyte during a first time period, detecting when one or more of the received plurality of time spaced analyte related data crosses a predetermined analyte threshold level during the first time period, receiving a plurality of time spaced temperature data during the first time period, determining a rate of change of the received plurality of time spaced temperature data and detecting when the determined rate of change crosses a predetermined rate of temperature change; and asserting a notification when the determined rate of change of the received plurality of the time spaced temperature data reaches the predetermined rate of temperature change and when the one or more of the received plurality of time spaced analyte related data reaches the predetermined threshold analyte level during the first time period.

A method in accordance with another embodiment includes receiving a plurality of time spaced analyte related data monitored by an analyte sensor in fluid contact with an analyte during a first time period, detecting when one or more of the received plurality of time spaced analyte related data reaches a predetermined analyte threshold level during the first time period, receiving a plurality of time spaced temperature data during the first time period, detecting when one or more of the time spaced temperature related data crosses a predetermined threshold temperature level during the first time period, and asserting a notification when the one or more of the received plurality of time spaced analyte related data reaches a predetermined threshold analyte level and when the one or more of the plurality of time spaced temperature related data reaches the predetermined temperature threshold level during the first time period.

In still another aspect, a method in accordance with certain embodiments of the present disclosure includes monitoring a variation in on-skin temperature in proximity to a transcutaneously positioned analyte sensor having at least a portion in fluid contact with an analyte during a monitoring time period, detecting the variation in the monitored temperature exceeding a predetermined threshold level, confirming a presence of a medically significant condition when the detected variation in the monitored temperature exceeds the predetermined threshold level, and asserting a notification associated with the medically significant condition when it is confirmed, wherein confirming the presence of the medically significant condition includes determining a variation in the monitored analyte level exceeding the predetermined threshold level based on comparing a slope indicative of the change in the monitored analyte level substantially to a slope indicative of the change in the monitored on-skin temperature variation.

A method in still another embodiment includes detecting a concurrent occurrence of a decrease in monitored analyte level and a corresponding decrease in monitored on-skin temperature, confirming a presence of an impending hypoglycemic condition, and asserting a notification corresponding to the confirmed impending hypoglycemic condition.

A method of confirming hypoglycemic condition in a patient in yet still a further embodiment includes monitoring a directional change in glucose level based on data stream received from an analyte sensor during a monitoring time period, monitoring a directional change in a first physiological parameter during the monitoring time period, monitoring a directional change in a second physiological parameter during the monitoring time period, detecting an initialization of a hypoglycemic alarm based, at least in part, on the directional change of the monitored glucose level, and comparing the directional change in one or more of the first or the second physiological parameters relative to the directional change in the glucose level prior to the assertion of the hypoglycemic alarm.

An apparatus in accordance with one embodiment includes one or more processors, and a memory for storing instructions which, when executed by the one or more processors, causes the one or more processors to receive a plurality of time spaced analyte related data monitored by an analyte sensor in fluid contact with an analyte during a first time period, determine a rate of change of the received plurality of time spaced analyte related data, receive a plurality of time spaced temperature data during the first time period, determine a rate of change of the received plurality of time spaced temperature data, compare the determined rate of change of the received plurality of the time spaced temperature data to the predetermined threshold level when the determined rate of change of the received plurality of time spaced analyte related data exceeds a predetermined threshold level, and assert a notification when the determined rate of change of the received plurality of the time spaced temperature data exceeds the predetermined threshold level.

An apparatus in accordance with still another aspect includes one or more processors, and a memory for storing instructions which, when executed by the one or more processors, causes the one or more processors to monitor a variation in on-skin temperature in proximity to a transcutaneously positioned analyte sensor having at least a portion in fluid contact with an analyte during a monitoring time period, detect the variation in the monitored temperature exceeding a predetermined threshold level, confirm a presence of a medically significant condition when the detected variation in the monitored temperature exceeds the predetermined threshold level, and assert a notification associated with the medically significant condition when it is confirmed, wherein the memory for storing instructions which, when executed by the one or more processors, causes the one or more processors to determine a variation in the monitored analyte level exceeding the predetermined threshold level based on comparing a slope indicative of the change in the monitored analyte level substantially to a slope indicative of the change in the monitored on-skin temperature variation.

An apparatus in accordance with still another aspect includes one or more processors, and a memory for storing instructions which, when executed by the one or more processors, causes the one or more processors to detect a concurrent occurrence of a decrease in monitored analyte level and a corresponding decrease in monitored on-skin temperature, confirm a presence of an impending hypoglycemic condition, and assert a notification corresponding to the confirmed impending hypoglycemic condition.

An apparatus in still yet a further embodiment includes one or more processors, and a memory for storing instructions which, when executed by the one or more processors, causes the one or more processors to monitor a directional change in glucose level based on data stream received from an analyte sensor during a monitoring time period, monitor a directional change in a first physiological parameter during the monitoring time period, monitor a directional change in a second physiological parameter during the monitoring time period, detect an initialization of a hypoglycemic alarm based, at least in part, on the directional change of the monitored glucose level, and compare the directional change in one or more of the first or the second physiological parameters relative to the directional change in the glucose level prior to the assertion of the hypoglycemic alarm.

In this manner, in aspects of the present disclosure, the occurrence of false notifications associated with the presence of hypoglycemic condition, impending hypoglycemic condition, or onset of hypoglycemic condition is reduced, providing robustness to the glucose monitoring system.

These and other features, objects and advantages of the present disclosure will become apparent to those persons skilled in the art upon reading the details of the present disclosure as more fully described below.

BRIEF DESCRIPTION OF THE DRAWINGS

A detailed description of various aspects, features and embodiments of the present disclosure is provided herein with reference to the accompanying drawings, which are briefly described below. The drawings are illustrative and are not necessarily drawn to scale, with some components and features being exaggerated for clarity. The drawings illustrate various aspects or features of the present disclosure and may illustrate one or more embodiment(s) or example(s) of the present disclosure in whole or in part. A reference numeral, letter, and/or symbol that is used in one drawing to refer to a particular element or feature may be used in another drawing to refer to a like element or feature. Included in the drawings are the following.

INCORPORATION BY REFERENCE

Figure 1:
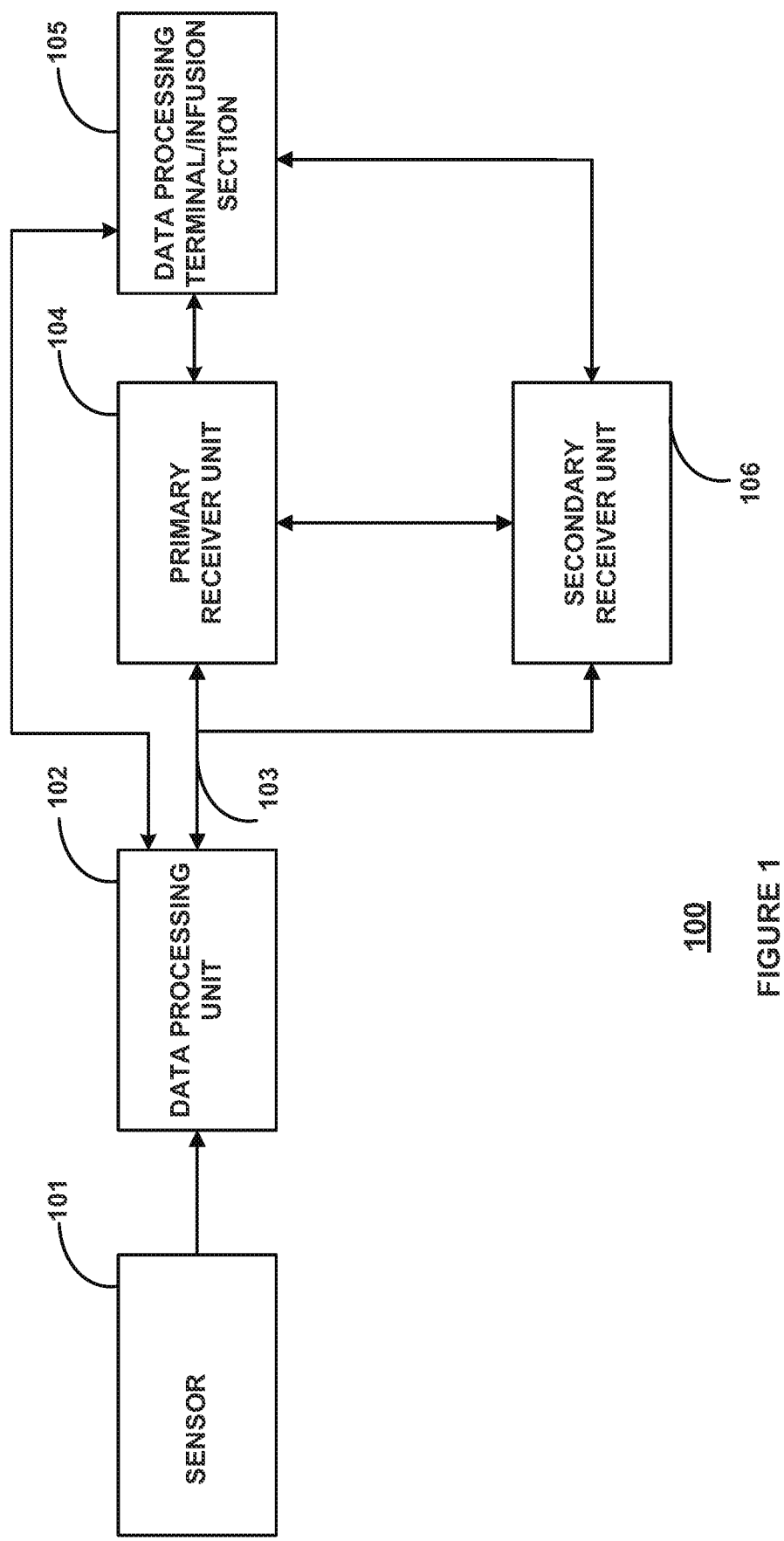
FIG. 1 shows a block diagram of an embodiment of a data monitoring and management system with which a sensor according to the present disclosure is usable.

Patents, applications and/or publications described herein, including the following patents, applications and/or publications are incorporated herein by reference for all purposes: U.S. Pat. Nos. 4,545,382, 4,711,245, 5,262,035, 5,262,305, 5,264,104, 5,320,715, 5,356,786, 5,509,410, 5,543,326, 5,593,852, 5,601,435, 5,628,890, 5,820,551, 5,822,715, 5,899,855, 5,918,603, 6,071,391, 6,103,033, 6,120,676, 6,121,009, 6,134,461, 6,143,164, 6,144,837, 6,161,095, 6,175,752, 6,270,455, 6,284,478, 6,299,757, 6,338,790, 6,377,894, 6,461,496, 6,503,381, 6,514,460, 6,514,718, 6,540,891, 6,560,471, 6,579,690, 6,591,125, 6,592,745, 6,600,997, 6,605,200, 6,605,201, 6,616,819, 6,618,934, 6,650,471, 6,654,625, 6,676,816, 6,730,200, 6,736,957, 6,746,582, 6,749,740, 6,764,581, 6,773,671, 6,881,551, 6,893,545, 6,932,892, 6,932,894, 6,942,518, 7,041,468, 7,167,818, and 7,299,082, U.S. Published Application Nos. 2004/0186365, now U.S. Pat. No. 7,811,231, 2005/0182306, now U.S. Pat. No. 8,771,183, 2006/0025662, now U.S. Pat. No. 7,740,581, 2006/0091006, 2007/0056858, now U.S. Pat. No. 8,298,389, 2007/0068807, now U.S. Pat. No. 7,846, 311, 2007/0095661, 2007/0108048, now U.S. Pat. No. 7,918,975, 2007/0199818, now U.S. Pat. No. 7,811,430, 2007/0227911, now U.S. Pat. No. 7,887,682, 2007/0233013, 2008/0066305, now U.S. Pat. No. 7,895,740, 2008/ 0081977, now U.S. Pat. No. 7,618,369, 2008/0102441, now U.S. Pat. No. 7,822,557, 2008/0148873, now U.S. Pat. No. 7,802,467, 2008/0161666, 2008/0267823, and 2009/ 0054748, now U.S. Pat. No. 7,885,698, U.S. patent application Ser. Nos. 11/461,725, now U.S. Pat. No. 7,866,026, Ser. Nos. 12/131,012, 12/393,921, 12/242,823, now U.S. Pat. No. 8,219,173, Ser. No. 12/363,712, now U.S. Pat. No. 8,346,335, Ser. Nos. 12/495,709, 12/698,124, 12/698,129, 12/714,439, 12/794,721, now U.S. Pat. No. 8,595,607, Ser. Nos. 12/807,278, 12/842,013, and 12/871,901, now U.S. Pat. No. 8,514,086, and U.S. Provisional Application Nos. 61/238,646, 61/246,825, 61/247,516, 61/249,535, 61/317, 243, 61/345,562, 61/325,260 and 61/361,374.

DETAILED DESCRIPTION

Before the present disclosure is described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges as also encompassed within the disclosure, subject to any specifically excluded limit in the stated range. Where the stated range includes one or both of the limits, ranges excluding either or both of those included limits are also included in the disclosure.

It must be noted that as used herein and in the appended claims, the singular forms "a", "an", and "the" include plural referents unless the context clearly dictates otherwise.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Generally, embodiments of the present disclosure relate to methods and devices for detecting at least one analyte, such as glucose, in body fluid. Embodiments relate to the continuous and/or automatic in vivo monitoring of the level of one or more analytes using a continuous analyte monitoring system that includes an analyte sensor for the in vivo detection, of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a control unit, transmitter, receiver, transceiver, processor, etc. At least a portion of a sensor may be, for example, subcutaneously positionable in a patient for the continuous or semi-continuous monitoring of a level of an analyte in a patient's interstitial fluid. For the purposes of this description, semi-continuous monitoring and continuous monitoring will be used interchangeably, unless noted otherwise.

The sensor response may be correlated and/or converted to analyte levels in blood or other fluids. In certain embodiments, an analyte sensor may be positioned in contact with interstitial fluid to detect the level of glucose, which may be used to infer the glucose level in the patient's bloodstream. Analyte sensors may be insertable into a vein, artery, or other portion of the body containing fluid. Embodiments of the analyte sensors of the subject disclosure may be configured for monitoring the level of the analyte over a time period which may range from minutes, hours, days, weeks, or longer.

In aspects of the present disclosure, temperature, perspiration or other characteristics of a patient such as, for example, other measurable characteristics are monitored concurrently with the monitored analyte level, and used to, in one embodiment, either confirm or reject notifications associated with the medically significant condition such as the onset or impending hypoglycemic condition initially detected based on the monitored analyte level.

In one aspect, the hypoglycemic condition may be associated with a low blood glucose level such as, for example, 40-50 mg/dL or less (depending upon, for example, age, gender, and the like). Accordingly, alarms or notifications may be configured, as a default setting or programmed specific to each patient, to be triggered when the monitored glucose level decreases at a rate that approaches the hypoglycemic condition within a defined time period to enable the patient or the user (or the healthcare provider) to timely take corrective actions. For example, each alarm or notification may be programmed to be asserted or triggered when the monitored glucose level reaches approximately 80 to 100 mg/dL, and decreasing at a rate of 2 mg/dL/minute or more. Referring now to the Figures, an exemplary overall analyte monitoring system including the various components is described below.

FIG. 1 illustrates a data monitoring and management system such as, for example, an analyte (e.g., glucose) monitoring system 100 in accordance with certain embodiments. Embodiments of the subject disclosure are further described primarily with respect to glucose monitoring devices and systems, and methods of glucose detection, for convenience only and such description is in no way intended to limit the scope of the disclosure. It is to be understood that the analyte monitoring system may be configured to monitor a variety of analytes instead of or in addition to glucose, e.g., at the same time or at different times.

Analytes that may be monitored include, but are not limited to, acetyl choline, amylase, bilirubin, cholesterol, chorionic gonadotropin, creatine kinase (e.g., CK-MB), creatine, creatinine, DNA, fructosamine, glucose, glutamine, growth hormones, hormones, ketone bodies, lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

The analyte monitoring system 100 includes a sensor 101, a data processing unit 102 connectable to the sensor 101, and a primary receiver unit 104 which is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bi-directional communication. Further, the data processing unit 102 may include a transmitter or a transceiver to transmit and/or receive data to and/or from the primary receiver unit 104 and/or the data processing terminal 105 and/or optionally the secondary receiver unit 106.

The electrochemical sensors of the present disclosure may employ any suitable measurement technique, e.g., may detect current, may employ potentiometry, etc. Techniques may include, but are not limited to, amperometry, coulometry, and voltammetry. In some embodiments, sensing systems may be optical, colorimetric, and the like.

Also shown in FIG. 1 is an optional secondary receiver unit 106 which is operatively coupled to the communication link 103 and configured to receive data transmitted from the data processing unit 102. The secondary receiver unit 106 may be configured to communicate with the primary receiver unit 104, as well as the data processing terminal 105. The secondary receiver unit 106 may be configured for bi-directional wireless communication with each of the primary receiver unit 104 and the data processing terminal 105. As discussed in further detail below, in certain embodiments the secondary receiver unit 106 may be a de-featured receiver as compared to the primary receiver unit 104, i.e., the secondary receiver unit 106 may include a limited or minimal number of functions and features as compared with the primary receiver unit 104. As such, the secondary receiver unit 106 may include a smaller (in one or more, including all, dimensions), compact housing or embodied in a device such as a wrist watch, arm band, etc., for example.

Alternatively, the secondary receiver unit 106 may be configured with the same or substantially similar functions and features as the primary receiver unit 104. The secondary receiver unit 106 may include a docking portion to be mated with a docking cradle unit for placement by, e.g., the bedside for nighttime monitoring, and/or a bi-directional communication device. A docking cradle may recharge a power supply.

Only one sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105. Multiple sensors may be positioned in a patient for analyte monitoring at the same or different times. In certain embodiments, analyte information obtained by a first positioned sensor may be employed as a comparison to analyte information obtained by a second sensor. This may be useful to confirm or validate analyte information obtained from one or both of the sensors. Such redundancy may be useful if analyte information is contemplated in critical therapy-related decisions.

The analyte monitoring system 100 may be a continuous monitoring system or semi-continuous. In a multi-component environment, each component may be configured to be uniquely identified by one or more of the other components in the system so that communication conflict may be readily resolved between the various components within the analyte monitoring system 100. For example, unique identification codes (IDs), communication channels, and the like, may be used.

In certain embodiments, the sensor 101 is physically positioned in and/or on the body of a user whose analyte level is being monitored. The sensor 101 may be configured to continuously or semi-continuously sample the analyte level of the user automatically (without the user initiating the sampling), based on a programmed interval such as, for example, but not limited to, once every minute, once every five minutes and so on, and convert the sampled analyte level into a corresponding signal for transmission by the data processing unit 102. The data processing unit 102 is coupleable to the sensor 101 so that both devices are positioned in or on the user's body, with at least a portion of the analyte sensor 101 positioned transcutaneously. The data processing unit may include a fixation element such as adhesive or the like to secure it to the user's body. A mount (not shown) attachable to the user and mateable with the unit 102 may be used. For example, a mount may include an adhesive surface. The data processing unit 102 performs data processing functions, where such functions may include, but are not limited to, filtering and encoding of data signals, each of which corresponds to a sampled analyte level of the user, for transmission to the primary receiver unit 104 via the communication link 103. In one embodiment, the sensor 101 or the data processing unit 102 or a combined sensor/data processing unit may be wholly implantable under the skin layer of the user.

In certain embodiments, the primary receiver unit 104 may include a signal interface section including an RF receiver and an antenna that is configured to communicate with the data processing unit 102 via the communication link 103, and a data processing section for processing the received data from the data processing unit 102 such as data decoding, error detection and correction, data clock generation, data bit recovery, etc., or any combination thereof.

In operation, the primary receiver unit 104 in certain embodiments is configured to synchronize with the data processing unit 102 to uniquely identify the data processing unit 102, based on, for example, an identification information of the data processing unit 102, and thereafter, to continuously or semi-continuously receive signals transmitted from the data processing unit 102 associated with the monitored analyte levels detected by the sensor 101. Referring again to FIG. 1, the data processing terminal 105 may include a personal computer, a portable computer such as a laptop or a handheld device (e.g., personal digital assistants (PDAs), telephone such as a cellular phone (e.g., a multi-media and Internet-enabled mobile phone such as an iPhone, Blackberry device or similar phone), mp3 player, pager, global position system (GPS)) drug delivery device, each of which may be configured for data communication with the receiver via a wired or a wireless connection. Additionally, the data processing terminal 105 may further be connected to a data network (not shown) for storing, retrieving, updating, and/or analyzing data corresponding to the detected analyte level of the user.

The data processing terminal 105 may include an infusion device such as an insulin infusion pump or the like, which may be configured to administer insulin to patients, and which may be configured to communicate with the primary receiver unit 104 for receiving, among others, the measured analyte level. Alternatively, the primary receiver unit 104 may be configured to integrate an infusion device therein so that the primary receiver unit 104 is configured to administer insulin (or other appropriate drug) therapy to patients, for example, for administering and modifying basal profiles, as well as for determining appropriate boluses for administration based on, among others, the detected analyte levels received from the data processing unit 102. An infusion device may be an external device or an internal device (wholly implantable in a user).

In certain embodiments, the data processing terminal 105, which may include an insulin pump, may be configured to receive the analyte signals from the data processing unit 102, and thus, incorporate the functions of the primary receiver unit 104 including data processing for managing the patient's insulin therapy and analyte monitoring. In certain embodiments, the communication link 103 as well as one or more of the other communication interfaces shown in FIG. 1, may use one or more of an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements), while avoiding potential data collision and interference.

Figure 2:
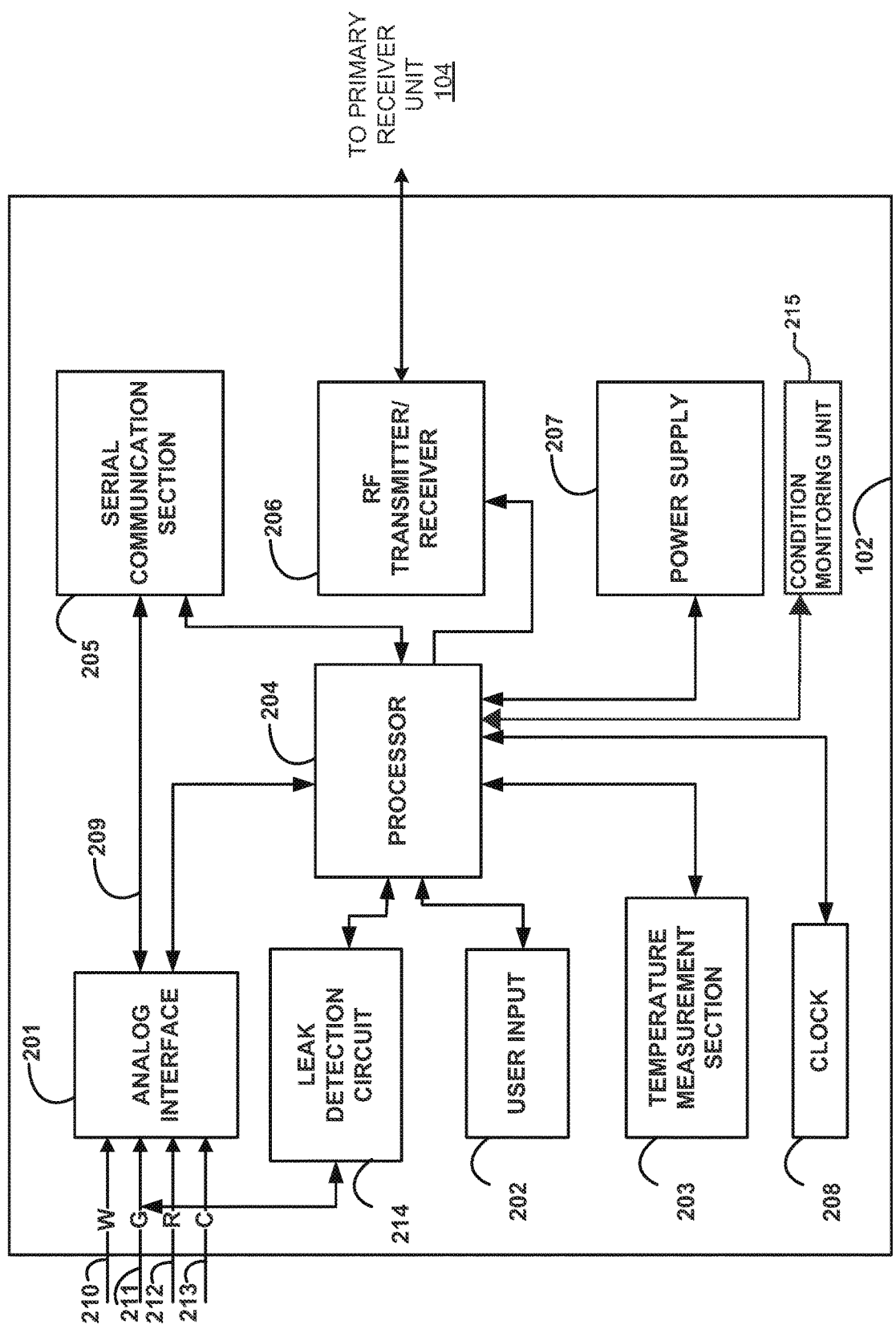
FIG. 2 shows a block diagram of an embodiment of the data processing unit of the data monitoring and management system of FIG. 1.

FIG. 2 shows a block diagram of an embodiment of a data processing unit of the data monitoring and detection system shown in FIG. 1. The data processing unit 102 thus may include one or more of an analog interface 201 configured to communicate with the sensor 101 (FIG. 1), a user input 202, and a temperature measurement section 203, each of which is operatively coupled to a processor 204 such as a central processing unit (CPU). User input and/or interface components may be included or a data processing unit may be free of user input and/or interface components. In certain embodiments, one or more application-specific integrated circuits (ASIC) may be used to implement one or more functions or routines associated with the operations of the data processing unit (and/or receiver unit) using for example one or more state machines and buffers.

Further shown in FIG. 2 are a transmitter serial communication section 205 and an RF transmitter 206, each of which is also operatively coupled to the processor 204. The RF transmitter 206, in some embodiments, may be configured as an RF receiver or an RF transmitter/receiver, such as a transceiver, to transmit and/or receive data signals. Moreover, a power supply 207, such as a battery, may also be provided in the data processing unit 102 to provide the necessary power for the data processing unit 102. Additionally, as can be seen from the Figure, clock 208 may be provided to, among others, supply real time information to the processor 204.

As can be seen in the embodiment of FIG. 2, the sensor 101 (FIG. 1) includes four contacts, three of which are electrodes—working electrode (W) 210, guard contact (G) 211, reference electrode (R) 212, and counter electrode (C) 213, each operatively coupled to the analog interface 201 of the data processing unit 102. In certain embodiments, each of the working electrode (W) 210, guard contact (G) 211, reference electrode (R) 212, and counter electrode (C) 213 may be made using a non-corroding conductive material that may be applied by, e.g., chemical vapor deposition (CVD), physical vapor deposition, sputtering, reactive sputtering, printing, coating, ablating (e.g., laser ablation), painting, dip coating, etching, and the like. Materials include, but are not limited to, carbon (such as graphite), gold, iridium, ruthenium, palladium, platinum, rhenium, rhodium, silver, mixtures thereof, and alloys thereof, and metallic oxides, like ruthenium dioxide or iridium dioxide, of these elements.

In certain embodiments, a unidirectional input path is established from the sensor 101 (FIG. 1) and/or manufacturing and testing equipment to the analog interface 201 of the data processing unit 102, while a unidirectional output is established from the output of the RF transmitter 206 of the data processing unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in certain embodiments, via the data path described above, the data processing unit 102 is configured to transmit to the primary receiver unit 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the data processing unit 102 for operation upon completion of the manufacturing process as well as for direct communication for diagnostic and testing purposes.

The processor 204 may be configured to transmit control signals to the various sections of the data processing unit 102 during the operation of the data processing unit 102. In certain embodiments, the processor 204 also includes memory (not shown) for storing data such as the identification information for the data processing unit 102, as well as the data signals received from the sensor 101. The stored information may be retrieved and processed for transmission to the primary receiver unit 104 under the control of the processor 204. Furthermore, the power supply 207 may include a commercially available battery.

The data processing unit 102 is also configured such that the power supply section 207 is capable of providing power to the data processing unit 102 for a minimum period of time, e.g., at least about one month, e.g., at least about three months or more, of continuous operation. The minimum time period may be after (i.e., in addition to), a period of time, e.g., up to about eighteen months, of being stored in a low- or no-power (non-operating) mode. In certain embodiments, this may be achieved by the processor 204 operating in low power modes in the non-operating state, for example, drawing no more than minimal current, e.g., approximately 1 µA of current or less. In certain embodiments, a manufacturing process of the data processing unit 102 may place the data processing unit 102 in the lower power, non-operating state (i.e., post-manufacture sleep mode). In this manner, the shelf life of the data processing unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present disclosure, the power supply unit 207 is configured to provide the necessary power to each of the components of the data processing unit 102 shown in FIG. 2.

Referring back to FIG. 2, the power supply section 207 of the data processing unit 102 in one embodiment may include a rechargeable battery unit that may be recharged by a separate power supply recharging unit (for example, provided in the receiver unit 104) so that the data processing unit 102 may be powered for a longer period of usage time. In certain embodiments, the data processing unit 102 may be configured without a battery in the power supply section 207, in which case the data processing unit 102 may be configured to receive power from an external power supply source (for example, a battery, electrical outlet, etc.) as discussed in further detail below.

Referring yet again to FIG. 2, a temperature detection section 203 of the data processing unit 102 is configured to monitor the temperature of the skin near the sensor insertion site. The temperature reading may be used to adjust the analyte readings obtained from the analog interface 201. In a further aspect, the temperature measurement or reading generated from the temperature detection section 203 may be used in conjunction with the received analyte data to determine or confirm a monitored condition such as an impending or onset of hypoglycemic condition as discussed in further detail below. For example, the temperature measurement section may include a thermistor to monitor the on-skin (or ambient) temperature in direct or indirect contact with the patient's skin. Example embodiments of temperature measurement section are provided in, for example, U.S. Pat. No. 6,175,752, and application Ser. No. 11/026,766 entitled "Method and Apparatus for Providing Temperature Sensor Module in a Data Communication System," each assigned to the assignee of the present application, and the disclosure of each of which are incorporated herein by reference for all purposes.

In a further embodiment, the temperature measurement or reading may be generated or determined from a different area of the body such as the ear canal, rectum, mouth, other body cavity, or forehead using a suitable temperature measuring device or components which incorporate the temperature measurement functionalities and capable of transmitting (wirelessly or via wired connection) the determined temperature information to the receiver unit 104/106 (FIG. 1) and/or data processing terminal/infusion section 105 (FIG. 1) for further processing.

Referring back to FIG. 2, the data processing unit 102 may also include a condition monitoring unit 215 in signal communication with the processor 204, and configured to monitor one or more physiological or other characteristics of the patient or the user of the data processing unit 102. For example, the perspiration level may be monitored by the condition monitoring unit 215 in one embodiment by detecting or determining conductance signal levels that vary depending upon the presence or absence of perspiration on skin, for example, using electrodes or probes or contacts on the skin of the patient. In one aspect, the electrodes, probes or contacts to determine or monitor the one or more physiological characteristics such as level of perspiration may be provided on the housing of the data processing unit 102, or alternatively, may be provided as a separate unit that is configured to provide or transfer the monitored characteristics information or data to the processor 204 of the data processing unit 102. Accordingly, in one aspect, the microprocessor based logic provided to the processor 204 may be configured to process the detected conductance signal levels to determine the presence of absence of perspiration and/or, to determine the level of and change in perspiration based on, for example, monitored or detected conductance signal level.

Referring back to FIG. 2, the RF transmitter 206 of the data processing unit 102 may be configured for operation in a certain frequency band, e.g., the frequency band of 315 MHz to 322 MHz, for example, in the United States. The operating frequency band may vary depending upon the location of use, communication protocol used, components used to implement the RF communication, and accordingly, the present disclosure contemplates varying ranges of operating frequency bands. Further, in certain embodiments, the RF transmitter 206 is configured to modulate the carrier frequency by performing, e.g., Frequency Shift Keying and Manchester encoding, and/or other protocol(s). In certain embodiments, the data transmission rate is set for efficient and effective transmission. For example, in certain embodiments the data transmission rate may be about 19,200 symbols per second, with a minimum transmission range for communication with the primary receiver unit 104.

Also shown is a leak detection circuit 214 coupled to the guard contact (G) 211 and the processor 204 in the data processing unit 102 of the data monitoring and management system 100. The leak detection circuit 214 may be configured to detect leakage current in the sensor 101 to determine whether the measured sensor data is corrupt or whether the measured data from the sensor 101 is accurate. Such detection may trigger a notification to the user.

Figure 3:
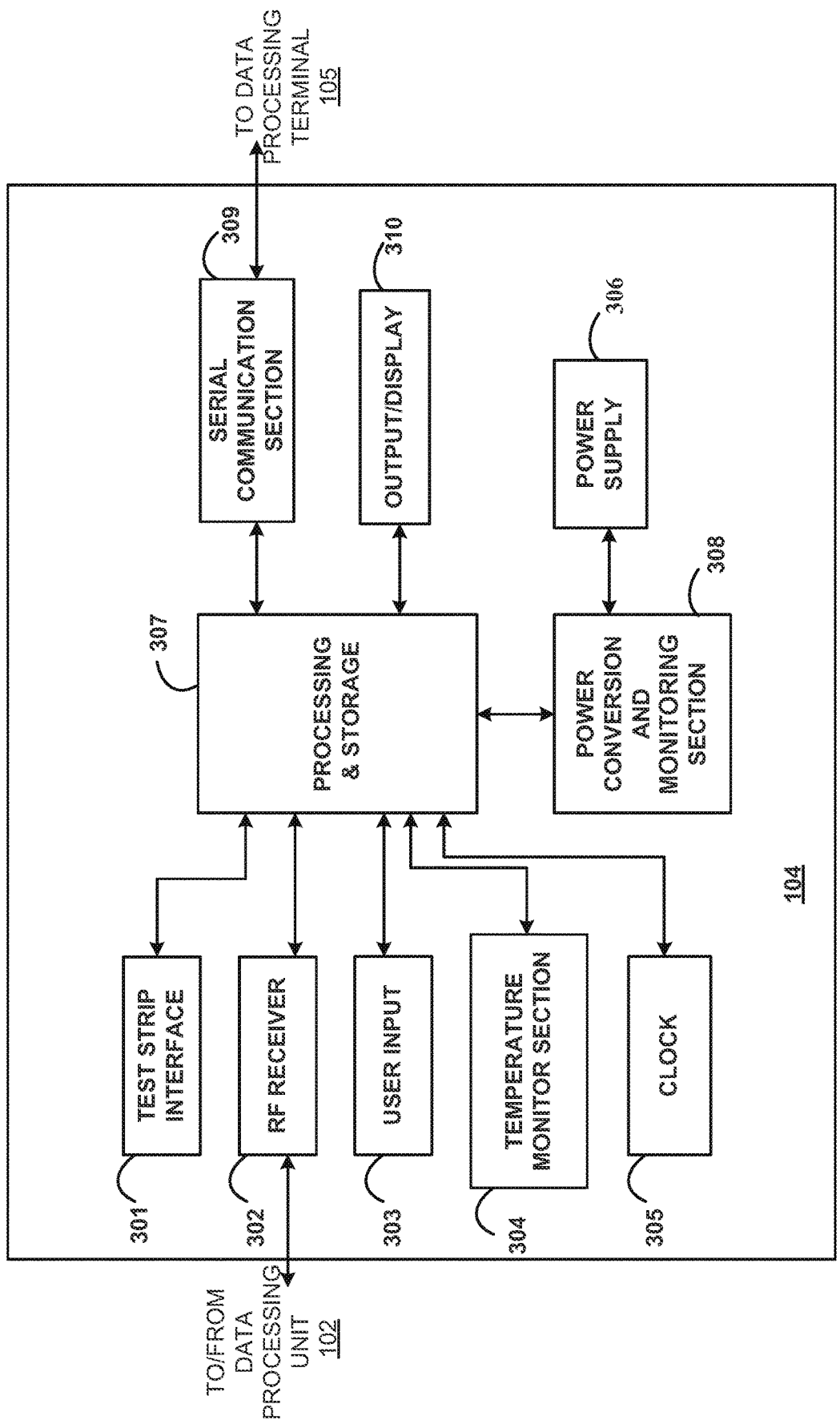
FIG. 3 shows a block diagram of an embodiment of the receiver/monitor unit of the data monitoring and management system of FIG. 1.

FIG. 3 shows a block diagram of an embodiment of a receiver/monitor unit such as the primary receiver unit 104 of the data monitoring and management system shown in FIG. 1. The primary receiver unit 104 may include one or more of: a blood glucose test strip interface 301 for in vitro testing, an RF receiver 302, an input 303, a temperature detection section 304, and a clock 305, each of which is operatively coupled to a processing and storage section 307. The primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the processing and storage unit 307. The receiver may include user input and/or interface components or may be free of user input and/or interface components.

In certain embodiments having a test strip interface 301, the interface includes a glucose level testing portion to receive a blood (or other body fluid sample) glucose test or information related thereto. For example, the interface may include a test strip port to receive an in vitro glucose test strip. The device may determine the glucose level of the test strip, and optionally display (or otherwise report or output) the glucose level on the output 310 of the primary receiver unit 104. Any suitable test strip may be employed, e.g., test strips that only require a very small amount (e.g., one microliter or less, e.g., 0.5 microliter or less, e.g., 0.1 microliter or less), of applied sample to the strip in order to obtain accurate glucose information, e.g. FreeStyle® and Precision® blood glucose test strips from Abbott Diabetes Care Inc. Glucose information obtained by the in vitro glucose testing device may be used for a variety of purposes, computations, etc. For example, the information may be used to calibrate sensor 101 (however, calibration of the subject sensors may not be necessary), confirm results of the sensor 101 to increase the confidence thereof (e.g., in instances in which information obtained by sensor 101 is employed in therapy related decisions), etc. Exemplary blood glucose monitoring systems are described, e.g., in U.S. Pat. Nos. 6,071,391; 6,120,676; 6,338,790; and 6,616,819; and in U.S. application Ser. No. 11/282,001, now U.S. Pat. No. 7,918,975; and Ser. No. 11/225,659, now U.S. Pat. No. 8,298,389, the disclosures of which are herein incorporated by reference.

The RF receiver 302 is configured to communicate, via the communication link 103 (FIG. 1) with the RF transmitter 206 of the data processing unit 102, to receive encoded data signals from the data processing unit 102 for, among others, signal mixing, demodulation, and other data processing. The input 303 of the primary receiver unit 104 is configured to allow the user to enter information into the primary receiver unit 104 as needed. In one aspect, the input 303 may include keys of a keypad, a touch-sensitive screen, and/or a voice-activated input command unit, and the like. The temperature monitor section 304 is configured to provide temperature information of the primary receiver unit 104 to the receiver processing and storage unit 307, while the clock 305 provides, among others, real time information to the receiver processing and storage unit 307.

Each of the various components of the primary receiver unit 104 shown in FIG. 3 is powered by the power supply 306 (and/or other power supply) which, in certain embodiments, includes a battery. Furthermore, the power conversion and monitoring section 308 is configured to monitor the power usage by the various components in the primary receiver unit 104 for effective power management and may alert the user, for example, in the event of power usage which renders the primary receiver unit 104 in sub-optimal operating conditions. An example of such sub-optimal operating condition may include, for example, operating the vibration output mode (as discussed below) for a period of time thus substantially draining the power supply 306 while the processing and storage unit 307 (thus, the primary receiver unit 104) is turned on. Moreover, the power conversion and monitoring section 308 may additionally be configured to include a reverse polarity protection circuit such as a field effect transistor (FET) configured as a battery activated switch.

The serial communication section 309 in the primary receiver unit 104 is configured to provide a bi-directional communication path from the testing and/or manufacturing equipment for, among others, initialization, testing, and configuration of the primary receiver unit 104. Serial communication section 309 can also be used to upload data to a computer, such as time-stamped blood glucose data. The communication link with an external device (not shown) can be made, for example, by cable, infrared (IR) or RF link. The output 310 of the primary receiver unit 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones, pagers, etc. In certain embodiments, the primary receiver unit 104 also includes an electro-luminescent lamp configured to provide backlighting to the output 310 for output visual display in dark ambient surroundings.

Referring back to FIG. 3, the primary receiver unit 104 may also include a storage section such as a programmable, non-volatile memory device as part of the processing and storage unit 307, or provided separately in the primary receiver unit 104, operatively coupled to the processor. The processing and storage unit 307 may be configured to perform Manchester decoding (or other protocol(s)) as well as error detection and correction upon the encoded data signals received from the data processing unit 102 via the communication link 103.

In further embodiments, the data processing unit 102 and/or the primary receiver unit 104 and/or the secondary receiver unit 106, and/or the data processing terminal/infusion section 105 may be configured to receive the blood glucose value from a wired connection or wirelessly over a communication link from, for example, a blood glucose meter. In further embodiments, a user manipulating or using the analyte monitoring system 100 (FIG. 1) may manually input the blood glucose value using, for example, a user interface (for example, a keyboard, keypad, voice commands, and the like) incorporated in the one or more of the data processing unit 102, the primary receiver unit 104, secondary receiver unit 106, or the data processing terminal/infusion section 105.

In certain embodiments, the data processing unit 102 (FIG. 1) is configured to detect the current signal from the sensor 101 (FIG. 1) and optionally the skin and/or ambient temperature near the sensor 101, which may be preprocessed by, for example, the data processing unit processor 204 (FIG. 2) and transmitted to the receiver unit (for example, the primary receiver unit 104 (FIG. 1)) at least at a predetermined time interval, such as for example, but not limited to, once per minute, once every two minutes, once every five minutes, or once every ten minutes. Although specific time frames have been mentioned, it is contemplated that the predetermined time interval may correspond to any amount of time selected by the patient, user or healthcare provider. Additionally, the data processing unit 102 may be configured to perform sensor insertion detection and data quality analysis, information pertaining to which may also be transmitted to the receiver unit 104 periodically at the predetermined time interval. In turn, the receiver unit 104 may be configured to perform, for example, skin temperature compensation as well as calibration of the sensor data received from the data processing unit 102.

Additional detailed descriptions are provided in U.S. Pat. Nos. 5,262,035; 5,262,035; 5,264,104; 5,262,305; 5,320,715; 5,593,852; 6,103,033; 6,134,461; 6,175,752; 6,560,471; 6,579,690; 6,605,200; 6,654,625; 6,746,582; and 6,932,894; and in U.S. Published Patent Application No. 2004/0186365, now U.S. Pat. No. 7,811,231, the disclosures of which are herein incorporated by reference. Description of exemplary methods for forming the sensor is provided in U.S. patents and applications noted herein, including U.S. Pat. Nos. 5,262,035; 6,103,033; 6,175,752; and 6,284,478, the disclosures of which are herein incorporated by reference. Examples of sensing layers that may be employed are described in U.S. patents and applications noted herein, including, e.g., in U.S. Pat. Nos. 5,262,035; 5,264,104; 5,543,326; 6,605,200; 6,605,201; 6,676,819; and 7,299,082; the disclosures of which are herein incorporated by reference.

The subject analyte measurement systems may include an alarm system that, e.g., based on information from a processor, warns the patient of a potentially detrimental condition of the analyte. For example, if glucose is the analyte, an alarm system may warn a user of conditions such as hypoglycemia and/or hyperglycemia and/or impending hypoglycemia, and/or impending hyperglycemia. An alarm system may be triggered when analyte levels approach, reach or exceed a threshold value. An alarm system may also, or alternatively, be activated when the rate of change, or the acceleration of the rate of change in the analyte level increase or decrease, approaches, reaches or exceeds a threshold rate or acceleration. A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

The subject disclosure also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

Figure 4:
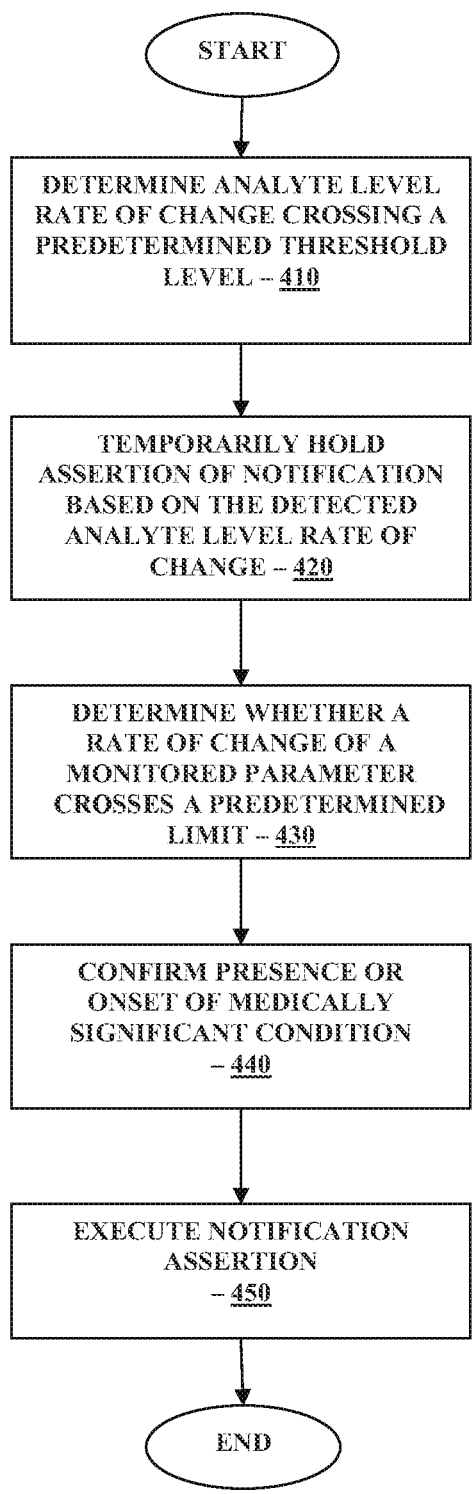
FIG. 4 is a flowchart illustrating a routine associated with determining false signal attenuation of an analyte sensor in one aspect of the present disclosure.

Referring back to the Figures, FIG. 4 is a flowchart illustrating a routine associated with determining false signal attenuation of an analyte sensor in one aspect of the present disclosure. As shown, in one embodiment, a rate of change of analyte level such as monitored glucose level variation is determined or compared against a predetermined threshold level (410). In one aspect, the predetermined threshold level may be pre-programmed and stored in a memory storage device of the data processing unit 102 (FIG. 1) and/or the processing and storage unit 307 (FIG. 3) of the receiver 104/106. In other aspects, the predetermined threshold level may be programmable or adjustable by the user or the healthcare provider. In still a further aspect, the predetermined threshold level may include a plurality of threshold levels, each corresponding to a particular time of day (for example, day time, meal time, or night time) or an event such as exercise, meal, sleeping, intake of medication and the like.

Referring again to FIG. 4, when it is determined that the rate of change of the monitored analyte level crosses a predetermined threshold level (410) (for example, by exceeding an upper threshold level, or by falling below a lower threshold level), a temporary hold assertion function is called and executed to temporarily hold the assertion of a programmed notification based on the detected analyte level rate of change (420). That is, in one aspect, when an alarm or alert notification is programmed to be asserted based on the analyte level rate of change crossing the predetermined threshold, before the assertion of the alarm or alert notification is implemented, the receiver 104 or the data processing unit 102 may be programmed to execute a hold function to temporarily hold off the assertion of the alarm/alert notification.

Thereafter, as shown in FIG. 4, a rate of change or variation of another monitored parameter is compared against a predetermined limit (pre-programmed or adjusted by the user or the healthcare provider) to determine whether the rate of change of the monitored parameter crosses the predetermined limit (430). That is, in one aspect, a monitored temperature and/or perspiration level is retrieved and the rate of change of the temperature level is determined and compared against the predetermined limit. In one aspect, the time period of determining the rate of change of the monitored parameter is programmed or set to coincide with the time period of the monitored analyte level (based on which the alarm/alert notification is initiated). While the level of temperature or perspiration is described above as the monitored parameter which is determined upon detection of an alarm/alert notification based on the analyte level rate of change, within the scope of the present disclosure, other physiological and/or environmental parameters may be determined or analyzed individually, or in combination with one or more of the temperature level or the perspiration level.

Based on the determination of whether the rate of change of the monitored parameter crosses the predetermined limit (430), the presence/absence or onset of a medically significant condition associated with the alarm/alert notification discussed above, is confirmed (440), and thereafter upon confirmation of the presence of the medically significant condition, the hold assertion function is removed and the alarm/alert notification is output to, for example, notify the user or the healthcare provider (450). In one embodiment, the alarm/alert notification may include one or more of an audible notification (a discrete sound or a series of sounds or tones that either vary in intensity and/or output level), a vibratory notification (which may increase/decrease in the strength of vibration or be maintained at a steady vibration strength), or a visual notification (a numeric, graphical, textual or combinations thereof).

In this manner, in one aspect of the present disclosure, upon detection of a medically significant condition such as a hypoglycemic condition based on the monitored analyte levels, before any alarm or alert notification is output or presented to the user to take corrective actions, the detection of such condition is confirmed based on one or more other monitored parameters such as the level or variation of the user's body or on-skin temperature or the level or variation in perspiration. In this manner, the potential for a false positive indication of such alarm or alert condition determined based on the monitored analyte level alone may be reduced by confirmation of such condition based on other physiological and/or environmental parameters associated with the user.

Moreover, while hypoglycemia is described above, the medically significant condition may include other physiological conditions of the user where supplemental or additional monitored parameters are used to confirm the presence of the medically significant condition prior to notifying the user. Accordingly, the frequency of the false indication of the medically significant condition presence can be reduced and also, the user may be prevented from taking unnecessary corrective actions based on false indications of such condition.

Figure 5:
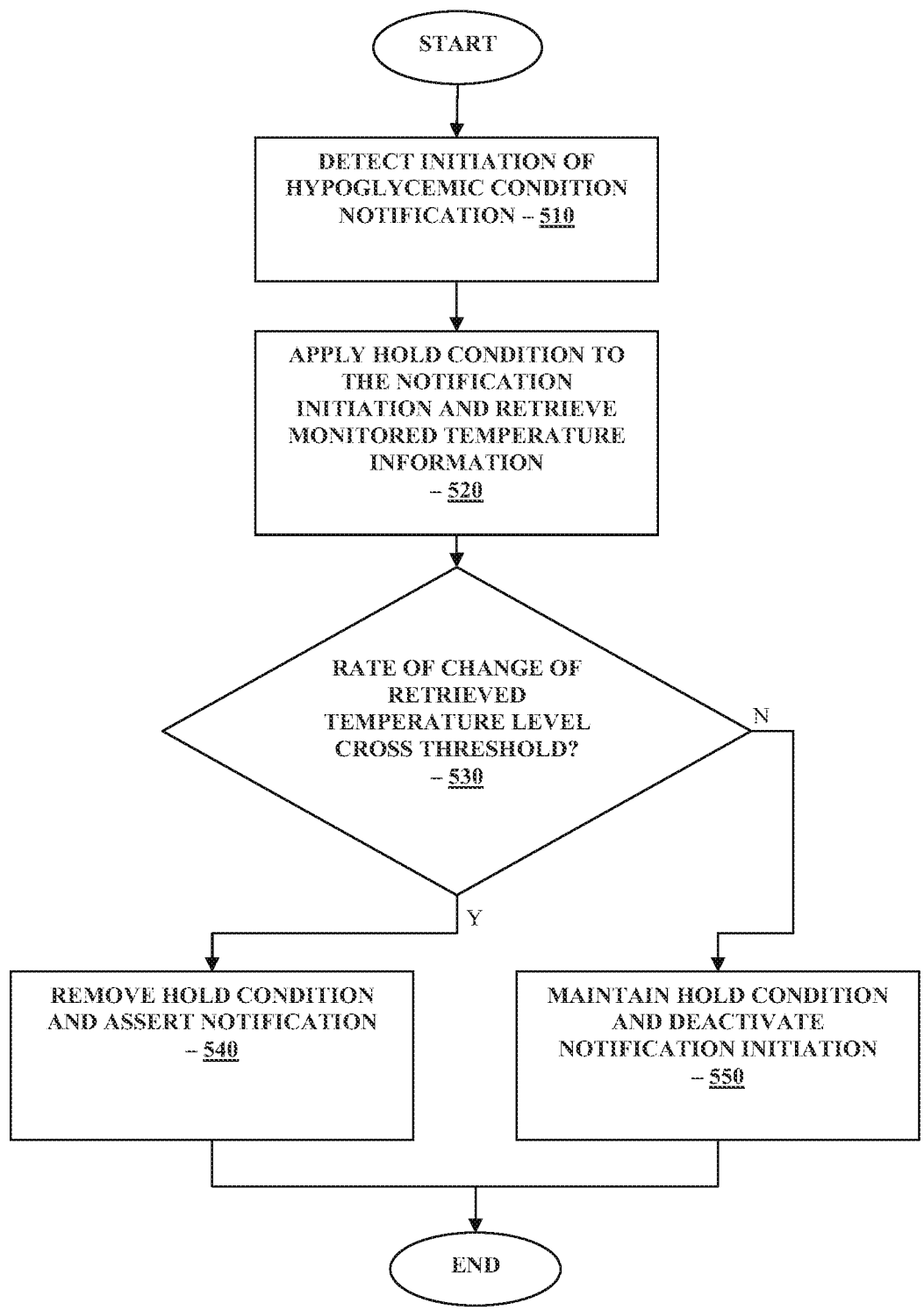
FIG. 5 is a flowchart illustrating a routine associated with determining false signal attenuation of an analyte sensor in another aspect of the present disclosure.

FIG. 5 is a flowchart illustrating a routine associated with determining false signal attenuation of an analyte sensor in another aspect of the present disclosure. Referring to the Figure, in one aspect, when the initiation of hypoglycemic condition notification is detected (510), a hold condition to the notification is applied and the monitored temperature information is retrieved (520). Thereafter, the rate of change of the retrieved temperature level is compared to a threshold level (530). If it is determined that the determined rate of temperature level change crosses the threshold (530), then the hold condition is removed and the initiated hypoglycemic notification is asserted (540). On the other hand, if the determined rate of temperature level change is determined to not have crossed the threshold (530), then the hold condition is maintained and the initiated hypoglycemic notification is deactivated (550).

Referring back to FIG. 5, when the monitored temperature information is retrieved (520), in one embodiment, the time period of the retrieved monitored temperature information is determined to substantially coincide with the time period of monitored analyte level based on which the hypoglycemic condition notification is initiated (510). In an alternate embodiment, the time period of the retrieved monitored temperature information may include the time period of the monitored analyte level such that the monitored temperature for processing and/or analysis spans a wider time period range.

Still alternatively, the time period of the monitored temperature information may be a subset of the time period of the monitored analyte level based on which the hypoglycemic condition notification is initiated. Indeed, the variation in the monitored time period as well as the number of available data sets for the monitored temperature level and the monitored analyte level may vary based on one or more of the frequency of data sampling, the availability of the information, the degree of sensitivity of the temperature detection (e.g., thermistor), and the like.

Figure 6:
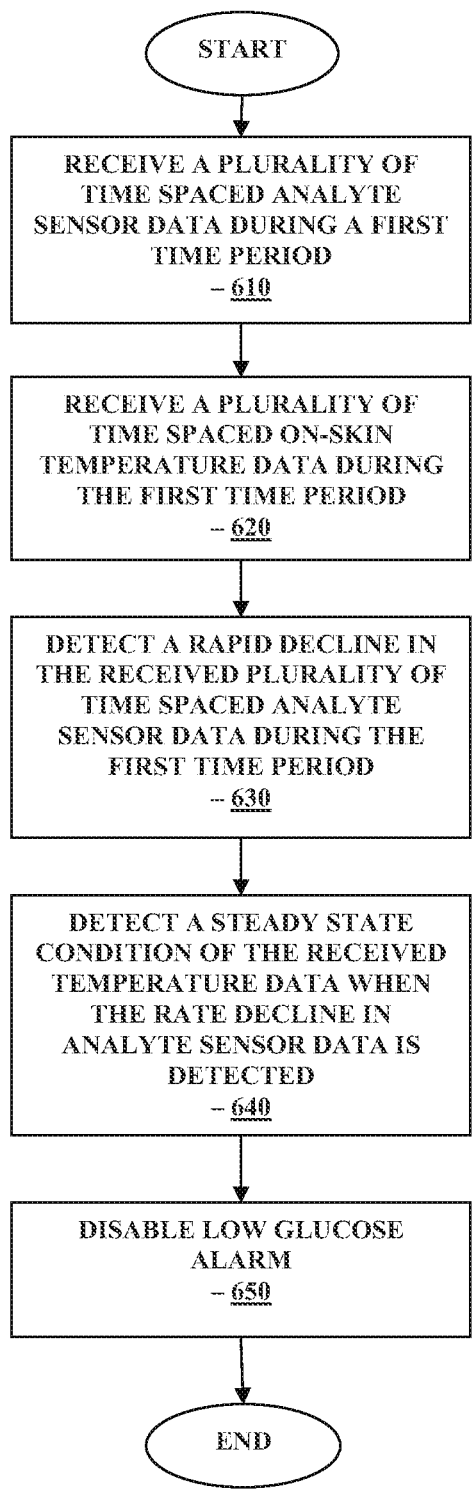
FIG. 6 is a flowchart illustrating a routine associated with determining false signal attenuation of an analyte sensor in a further aspect of the present disclosure.

FIG. 6 is a flowchart illustrating a routine associated with determining false signal attenuation of an analyte sensor in a further aspect of the present disclosure. As shown, in one embodiment, a plurality of time spaced analyte sensor data during a first time period is received (610). Thereafter, a plurality of time spaced on-skin temperature data during the first time period is received (620). Upon detection of a rapid decline in the received plurality of time spaced analyte sensor data during the first time period (630), the plurality of time spaced on-skin temperature data is analyzed. In one aspect, rapid decline in the received plurality of time spaced analyte sensor data may include a rate of change of the analyte sensor data at or greater than 2 mg/dL/min. Within the scope of the present disclosure, the rapid decline may include other variations of the rate of change that is greater or less than 2 mg/dL/min. Furthermore, while on skin temperature level monitoring and detection is described above, in accordance with aspects of the present disclosure, any suitable body temperature may be measured and used to confirm or reject the preliminary indication of a hypoglycemic condition.

Referring back to FIG. 6, upon detection of a steady state condition of the received plurality of time spaced temperature data during the first time period (640), low glucose alarm function (for example, in the data processing unit 102 and/or the receiver unit 104/106, or the data processing terminal/infusion section 105) is disabled (650) indicating that the detected rapid decline in the received plurality of time spaced analyte sensor data during the first time period (630) is not associated with a low glucose condition (or glucose level trending towards a low glucose condition), but rather, a false indication of the low glucose condition or an analyte sensor signal attenuation which may be attributable to parameters associated with the analyte sensor (e.g., unstable sensor), errors in data processing, dislodged sensor or the like. In one aspect, the steady state condition of the received plurality of time spaced temperature data may include variation of the temperature data during the first time period that does not cross a predetermined or preset level. That is, a steady state condition may include a relatively stable temperature information or level during the first time period.

While monitoring glucose level in addition to monitoring and determining temperature and/or perspiration level as described in conjunction with the various aspects of the present disclosure, other physiological parameters may be monitored and used to confirm or reject the occurrence of hypoglycemic condition. For example, palpitation or variation in heart rate may be monitored using, for example, a heart rate monitor, or the oxygen saturation level may be monitored using, for example, a pulse oximeter, to confirm or reject the occurrence of hypoglycemic condition indicated by the monitored glucose levels. Additional description of pulse oximetry for monitoring oxygen saturation level is provided in U.S. Pat. Nos. 6,606,511 and 6,912,413, disclosures of each of which are incorporated herein by reference. Furthermore, description of heart rate monitors for monitoring the heart rate is provided in U.S. Pat. No. 6,549,756, the disclosure of which is incorporated herein by reference.

Additionally, tremor may be monitored to confirm the detection of hypoglycemic condition where a variation in the movement may be used to confirm or reject the occurrence of hypoglycemic condition. Additional description of detecting tremor is provided in U.S. Pat. No. 5,293,879, the disclosure of which is incorporated herein by reference. Accordingly, when the monitored glucose level received from the analyte sensor indicates a hypoglycemic condition (or an impending hypoglycemic condition), a detection or variation of one or more of tremor, palpitation, perspiration, temperature or other physiological parameters may be used to in conjunction with the sensor data confirm or reject the indication of hypoglycemic condition.

Figure 7:
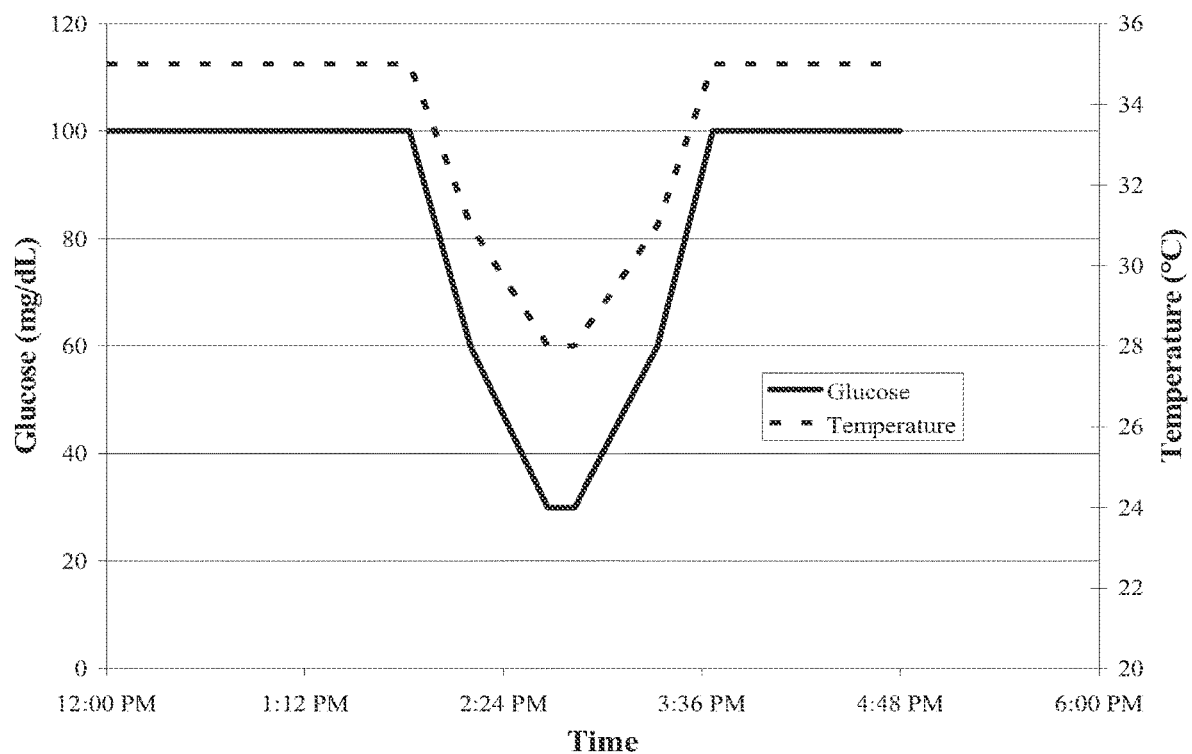
FIG. 7 is graphical illustration of the monitored glucose level and the corresponding temperature level during the same time period confirming a hypoglycemic event.
Figure 8:
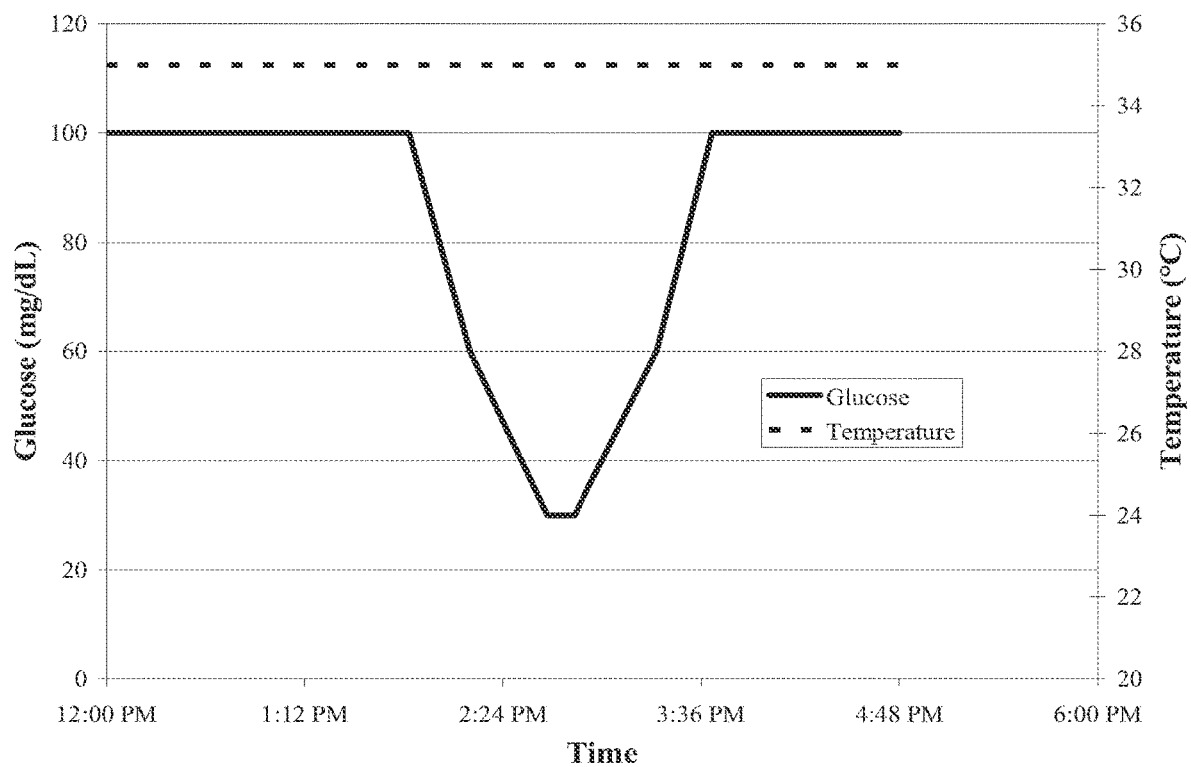
FIG. 8 is a graphical illustration of the monitored glucose level and the corresponding temperature level during the same time period indicating a false hypoglycemic event.

FIG. 7 is a graphical illustration of the monitored glucose level and the corresponding temperature level during the same time period confirming a hypoglycemic event. In contrast, FIG. 8 provides a graphical illustration of the monitored glucose level and the corresponding temperature level during the same time period indicating a false hypoglycemic event. As shown in these graphical illustrations, in aspects of the present disclosure, when an actual analyte sensor signal attenuation is detected (indicating a low glucose level), the level of the supplemental or additional parameter such as the temperature level is similar attenuated providing a level of correlation between the direction of change of the analyte level and the temperature level (as shown in FIG. 7).

On the other hand, as shown in FIG. 8, if the analyte sensor signal reported by the sensor is a false indication of the monitored analyte level, the corresponding level of the monitored additional parameter such as the temperature level does not provide the level of correlation as discussed above, but rather, indicates a deviation in the direction of change compared to the direction of change of the monitored analyte level.

In the manner described, in accordance with the various embodiments of the present disclosure, the occurrence of false alarms associated with analyte sensor signal attenuation may be minimized or mitigated by correlating the monitored analyte level with one or more additional parameters such as temperature or perspiration level. Accordingly, alarm or alert functions associated with monitored analyte levels in accordance with the present disclosure may be asserted when the underlying conditions associated with the alarm or alert function accurately reflects the monitored condition such that the user or the patient is not prompted to take unnecessary corrective actions based on false indication of the monitored condition.

The various processes described above including the processes operating in the software application execution environment in the analyte monitoring system 100 including the data processing unit 102, the receiver unit 104/106 or the data processing terminal/infusion section 105, performing one or more routines associated with the false analyte sensor signal attenuation determination described in conjunction with FIGS. 4-6, may be embodied as computer programs developed using an object oriented language that allows the modeling of complex systems with modular objects to create abstractions that are representative of real world, physical objects and their interrelationships. The software required to carry out the inventive process, which may be stored in a memory or storage device of the storage unit of the data processing unit 102, the receiver unit 104/106 or the data processing terminal/infusion section 105 in the analyte monitoring system 100, may be developed by a person of ordinary skill in the art and may include one or more computer program products.

In one embodiment, a method may include receiving a plurality of time spaced analyte related data monitored by an analyte sensor in fluid contact with an analyte during a first time period, detecting when one or more of the received plurality of time spaced analyte related data crosses a predetermined analyte threshold level during the first time period, receiving a plurality of time spaced temperature data during the first time period, determining a rate of change of the received plurality of time spaced temperature data, detecting when the determined rate of change crosses a predetermined rate of temperature change, and asserting a notification when the determined rate of change of the received plurality of the time spaced temperature data reaches the predetermined rate of temperature change and when the one or more of the received plurality of time spaced analyte related data reaches the predetermined threshold analyte level during the first time period.

A further embodiment may include determining when the monitored analyte level based on the received plurality of time spaced analyte related data indicates approaching the predetermined analyte threshold level during a second time period.

The first time period may precede the second time period.

The asserted notification may include one or more of an audible alert, a vibratory alert, a visual alert, or one or more combinations thereof.

The predetermined analyte threshold level may be associated with one of an impending hypoglycemic condition or an onset of hypoglycemic condition.

Another aspect may include determining a rate of change of the received plurality of time spaced analyte related data and comparing a slope of the determined rate of change of the received plurality of time spaced analyte related data to a slope of the rate of change of the received plurality of time spaced temperature data.

The slope of the determined rate of change of the received plurality of analyte related data and the slope of the rate of change of the received plurality of time spaced temperature data may be coincident.

The asserted notification may include an impending hypoglycemic condition.

Yet another aspect may include when the determined rate of change of the received plurality of the time spaced temperature data does not exceed the predetermined rate of temperature change, deactivating a notification function.

The deactivated notification function may include a hypoglycemic alarm.

Another embodiment may comprise receiving a plurality of time spaced analyte related data monitored by an analyte sensor in fluid contact with an analyte during a first time period, detecting when one or more of the received plurality of time spaced analyte related data crosses a predetermined analyte threshold level during the first time period, receiving a plurality of time spaced temperature data during the first time period, detecting when one or more of the time spaced temperature related data crosses a predetermined threshold temperature level during the first time period, and asserting a notification when the one or more of the received plurality of time spaced analyte related data reaches a predetermined threshold analyte level and when the one or more of the plurality of time spaced temperature related data reaches the predetermined temperature threshold level during the first time period.

Another embodiment may further include determining when the monitored analyte level based on the received plurality of time spaced analyte related data indicates approaching the predetermined analyte threshold level during a second time period.

The first time period may precede the second time period.

The asserted notification may be associated with a medically significant condition.

The medically significant condition may include an impending hypoglycemic condition.

Yet another embodiment may comprise monitoring a variation in on-skin temperature in proximity to a transcutaneously positioned analyte sensor having at least a portion in fluid contact with an analyte during a monitoring time period, detecting the variation in the monitored temperature exceeding a predetermined threshold level, confirming a presence of a medically significant condition when the detected variation in the monitored temperature exceeds the predetermined threshold level, and asserting a notification associated with the medically significant condition when it is confirmed, wherein confirming the presence of the medically significant condition includes determining a variation in the monitored analyte level exceeding the predetermined threshold level based on comparing a slope indicative of the change in the monitored analyte level substantially to a slope indicative of the change in the monitored on-skin temperature variation.

In yet another embodiment, a method may comprise detecting a concurrent occurrence of a decrease in monitored analyte level and a corresponding decrease in monitored on-skin temperature, confirming a presence of an impending hypoglycemic condition, and asserting a notification corresponding to the confirmed impending hypoglycemic condition.

The decrease in the monitored analyte level may include a decrease exceeding approximately 2 mg/dL/minute.

The decrease in the monitored on-skin temperature may include a temperature decrease exceeding approximately 2° C./15 minutes.

Detecting the concurrent occurrence may include determining a rate of change of the monitored analyte level during a predetermined time period, determining a rate of change of the monitored on-skin temperature during the predetermined time period, and verifying the determined rate of change of the monitored analyte level and the determined rate of change of the monitored on-skin temperature exceeds a predetermined threshold level substantially at the same time.

In another embodiment, a method of confirming hypoglycemic condition in a patient may comprise monitoring a directional change in glucose level based on data stream received from an analyte sensor during a monitoring time period, monitoring a directional change in a first physiological parameter during the monitoring time period, monitoring a directional change in a second physiological parameter during the monitoring time period, detecting an initialization of a hypoglycemic alarm based, at least in part, on the directional change of the monitored glucose level, and comparing the directional change in one or more of the first or the second physiological parameters relative to the directional change in the glucose level prior to the assertion of the hypoglycemic alarm.

The first physiological parameter or the second physiological parameter may be one of a temperature level, a perspiration level, heart rate, detected tremor, or oxygen saturation level.

The hypoglycemic alarm may be asserted when the glucose level directional change and the first physiological parameter direction change are the same.

The alarm may be asserted only when the second physiological parameter directional change is opposite the first physiological parameter directional change.

The monitored directional change in glucose level may have a negative slope.

The monitored directional change in the first physiological parameter may have a negative slope, and further, the monitored directional change in the second physiological parameter may have a positive slope.

The monitoring time period may include approximately five days or seven days.

The hypoglycemic alarm initialization may be detected when the monitored directional change in glucose level exceeds a predetermined threshold.

The predetermined threshold may include a decreasing rate of glucose level of approximately 2 mg/dL/minute.

Comparing the directional change may include temporarily disabling the hypoglycemic alarm initialization based on the comparison.

The hypoglycemic alarm initialization may be disabled when the directional change of the first and second physiological parameters are the same.

The hypoglycemic alarm initialization may be disabled when the directional change of the monitored glucose level does not coincide with the directional change of either of the first and second physiological parameters.

In another embodiment, an apparatus may comprise one or more processors and a memory for storing instructions which, when executed by the one or more processors, causes the one or more processors to receive a plurality of time spaced analyte related data monitored by an analyte sensor in fluid contact with an analyte during a first time period, determine a rate of change of the received plurality of time spaced analyte related data, receive a plurality of time spaced temperature data during the first time period, determine a rate of change of the received plurality of time spaced temperature data, compare the determined rate of change of the received plurality of the time spaced temperature data to the predetermined threshold level when the determined rate of change of the received plurality of time spaced analyte related data exceeds a predetermined threshold level, and assert a notification when the determined rate of change of the received plurality of the time spaced temperature data exceeds the predetermined threshold level.

The asserted notification may include one or more of an audible alert, a vibratory alert, a visual alert, or one or more combinations thereof.

The predetermined threshold level may include 3% decrease between each adjacent time spaced analyte related data and 3% decrease between each adjacent time temperature data.

The determined rate of change of the received plurality of time spaced analyte related data and the determined rate of change of the received plurality of time spaced temperature data may be temporally coincident.

The asserted notification may be associated with a medically significant condition.

The medically significant condition may include an impending hypoglycemic condition.

The notification may be asserted only when the determined rate of change of the received plurality of time spaced temperature data and the determined rate of change of the received analyte related data exceeds the predetermined threshold level substantially at the same time during the first time period.

The first time period may correspond to an analyte sensor life.

A further aspect may include when the determined rate of change of the received plurality of the time spaced temperature data does not exceed the predetermined threshold level, deactivating a notification function configured to be asserted when the determined rate of change of the analyte related data exceeds the predetermined threshold level.

The deactivated notification function may include a hypoglycemic alarm.

In another embodiment, an apparatus may comprise one or more processors, and a memory for storing instructions which, when executed by the one or more processors, causes the one or more processors to monitor a variation in on-skin temperature in proximity to a transcutaneously positioned analyte sensor having at least a portion in fluid contact with an analyte during a monitoring time period, detect the variation in the monitored temperature exceeding a predetermined threshold level, confirm a presence of a medically significant condition when the detected variation in the monitored temperature exceeds the predetermined threshold level, and assert a notification associated with the medically significant condition when it is confirmed, wherein the memory for storing instructions which, when executed by the one or more processors, causes the one or more processors to determine a variation in the monitored analyte level exceeding the predetermined threshold level based on comparing a slope indicative of the change in the monitored analyte level substantially to a slope indicative of the change in the monitored on-skin temperature variation.

Yet another embodiment may include an apparatus comprising one or more processors, and a memory for storing instructions which, when executed by the one or more processors, causes the one or more processors to detect a concurrent occurrence of a decrease in monitored analyte level and a corresponding decrease in monitored on-skin temperature, confirm a presence of an impending hypoglycemic condition, and assert a notification corresponding to the confirmed impending hypoglycemic condition.

The decrease in the monitored analyte level may include a decrease exceeding approximately 2 mg/dL/minute.

The decrease in the monitored on-skin temperature may include a temperature decrease exceeding approximately 2° C./15 minutes.

The memory for storing instructions which, when executed by the one or more processors, may cause the one or more processors to determine a rate of change of the monitored analyte level during a predetermined time period, determine a rate of change of the monitored on-skin temperature during the predetermined time period, and verify the determined rate of change of the monitored analyte level and the determined rate of change of the monitored on-skin temperature exceeds a predetermined threshold level substantially at the same time.

In yet another embodiment, an apparatus may comprise one or more processors, and a memory for storing instructions which, when executed by the one or more processors, causes the one or more processors to monitor a directional change in glucose level based on data stream received from an analyte sensor during a monitoring time period, monitor a directional change in a first physiological parameter during the monitoring time period, monitor a directional change in a second physiological parameter during the monitoring time period, detect an initialization of a hypoglycemic alarm based, at least in part, on the directional change of the monitored glucose level, and compare the directional change in one or more of the first or the second physiological parameters relative to the directional change in the glucose level prior to the assertion of the hypoglycemic alarm.

The first physiological parameter or the second physiological parameter may be one of a temperature level, a perspiration level, heart rate, detected tremor, or oxygen saturation level.

The hypoglycemic alarm may be asserted when the glucose level directional change and the first physiological parameter directional change are the same.

The alarm may be asserted only when the second physiological parameter directional change is opposite the first physiological parameter directional change.

The monitored directional change in glucose level may have a negative slope.

The monitored directional change in the first physiological parameter may have a negative slope, and further, the monitored directional change in the second physiological parameter may have a positive slope.

The monitoring time period may include approximately five days or seven days.

The hypoglycemic alarm initialization may be detected when the monitored directional change in glucose level exceeds a predetermined threshold.

The predetermined threshold may include a decreasing rate of glucose level of approximately 2 mg/dL/minute.

The memory for storing instructions which, when executed by the one or more processors, may cause the one or more processors to temporarily disable the hypoglycemic alarm initialization based on the comparison.

The memory for storing instructions which, when executed by the one or more processors, may cause the one or more processors to disable the hypoglycemic alarm initialization when the directional change of the first and second physiological parameters are the same.

The memory for storing instructions which, when executed by the one or more processors, may cause the one or more processors to disable the hypoglycemic alarm initialization when the directional change of the monitored glucose level does not coincide with the directional change of either of the first and second physiological parameters.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A glucose monitoring device, comprising:
one or more processors; and
a memory storing instructions which, when executed by the one or more processors, cause the one or more processors to:
receive sensor data indicative of a glucose level from a glucose sensor when at least a portion of the glucose sensor is positioned in contact with a bodily fluid under a skin surface of a user;
determine a hypoglycemic condition of the user based on the glucose level;
apply, in response to determining the hypoglycemic condition, a hold condition to a notification for the hypoglycemic condition;
receive movement data collected by a second sensor, the movement data indicating movement of the user;
determine a change in the movement of the user based on the movement data;
confirm the determination of the hypoglycemic condition based on the change of the movement of the user;
remove, in response to confirming the hypoglycemic condition based on the change of the movement of the user, the hold condition associated with the notification for the hypoglycemic condition; and
output an indication of the confirmed hypoglycemic condition to a display, wherein the indication comprises the notification for the hypoglycemic condition.

2. The device of claim 1, wherein the movement of the user comprises a tremor.

3. The device of claim 1, wherein confirming the determination of the hypoglycemic condition further comprises adjusting the glucose level using the movement data.

4. The device of claim 1, wherein the hypoglycemic condition is an impending hypoglycemic condition.

5. The device of claim 1, wherein the indication of the confirmed hypoglycemic condition comprises an alarm based on the glucose level.

6. The device of claim 5, wherein the alarm is related to the hypoglycemic condition.

7. The device of claim 5, wherein the alarm or the alert is provided at least in part by removing the hold condition.

8. The device of claim 1, wherein the device communicates with a receiver via a wired or wireless connection.

9. The device of claim 1, wherein the device is connected to a data network for storing or retrieving the sensor data.

10. The device of claim 1, wherein the device further comprises a touch-sensitive display configured to receive an input by the user.

11. The device of claim 1, further comprises a data processing unit configured to receive and process the sensor data received from the glucose sensor.

12. The device of claim 1 comprising the memory storing instructions which, when executed by the one or more processors, cause the one or more processors to calibrate the sensor data received from the glucose sensor.

13. A glucose monitoring method, comprising:
receiving sensor data indicative of a glucose level from a glucose sensor when at least a portion of the glucose sensor is positioned in contact with a bodily fluid under a skin surface of a user;

determining a hypoglycemic condition of the user based on the glucose level;

applying, in response to determining the hypoglycemic condition, a hold condition to a notification for the hypoglycemic condition;

receiving movement data collected by a second sensor, the movement data indicating movement of the user;

determining a change in the movement of the user based on the movement data;

confirming the determination of the hypoglycemic condition based on the change of the movement of the user;

removing, in response to confirming the hypoglycemic condition based on the change of the movement of the user, the hold condition associated with the notification for the hypoglycemic condition; and outputting an indication of the confirmed hypoglycemic condition to a display, wherein the indication comprises the notification for the hypoglycemic condition.

14. The method of claim 13, wherein the movement of the user comprises a tremor.

15. The method of claim 13, wherein confirming the determination of the hypoglycemic condition further comprises adjusting the glucose level using the movement data.

16. The method of claim 13, wherein the hypoglycemic condition is an impending hypoglycemic condition.

17. The method of claim 13, wherein the indication of the confirmed hypoglycemic condition comprises an alarm based on the glucose level.

18. The method of claim 17, wherein the alarm is related to the hypoglycemic condition.

19. The method of claim 17, wherein the alarm or the alert is provided at least in part by removing the hold condition.

20. The method of claim 13, further comprising communicating the sensor data with a receiver via a wired or wireless connection.

21. The method of claim 13, further comprising calibrating the sensor data received from the glucose sensor.

* * * * *